United States Patent
Bishai et al.

(10) Patent No.: US 11,590,177 B2
(45) Date of Patent: *Feb. 28, 2023

(54) METHODS OF TREATING CANCER USING BACTERIA EXPRESSING C-DI-AMP

(71) Applicant: The Johns Hopkins University, Baltimore, MD (US)

(72) Inventors: William R. Bishai, Baltimore, MD (US); Ruchi Jain Dey, Baltimore, MD (US); Bappaditya Dey, Baltimore, MD (US); Laurene Cheung, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/953,162

(22) Filed: Nov. 19, 2020

(65) Prior Publication Data

US 2021/0145896 A1    May 20, 2021

Related U.S. Application Data

(62) Division of application No. 16/147,916, filed on Oct. 1, 2018, now Pat. No. 10,842,828, which is a division of application No. 15/550,434, filed as application No. PCT/US2016/017248 on Feb. 10, 2016, now Pat. No. 10,130,663.

(60) Provisional application No. 62/114,610, filed on Feb. 11, 2015.

(51) Int. Cl.
*A61K 35/74* (2015.01)
*A61K 39/04* (2006.01)
*A61K 39/00* (2006.01)
*A61K 48/00* (2006.01)

(52) U.S. Cl.
CPC .............. *A61K 35/74* (2013.01); *A61K 39/04* (2013.01); *A61K 48/00* (2013.01); *A61K 2039/522* (2013.01)

(58) Field of Classification Search
CPC .. A61K 2039/522; A61K 35/74; A61K 39/04; A61K 48/00
See application file for complete search history.

(56) References Cited

U.S. PATENT DOCUMENTS

| | | |
|---|---|---|
| 9,061,048 B2 | 6/2015 | Portnoy et al. |
| 9,498,527 B2 | 11/2016 | Fukasaka et al. |
| 9,549,944 B2 | 1/2017 | Dubensky, Jr. et al. |
| 9,580,713 B2 | 2/2017 | Breaker et al. |
| 9,695,212 B2 | 7/2017 | Dubensky, Jr. et al. |
| 9,724,408 B2 | 8/2017 | Dubensky, Jr. et al. |
| 9,770,467 B2 | 9/2017 | Dubensky, Jr. et al. |
| 10,130,663 B2 * | 11/2018 | Bishai ............... A61P 35/00 |
| 2002/0160502 A1 * | 10/2002 | Chung ............... C07K 14/4727 424/264.1 |
| 2012/0164107 A1 | 6/2012 | Portnoy et al. |
| 2014/0220057 A1 | 8/2014 | Okubo et al. |
| 2014/0220059 A1 | 8/2014 | Asari et al. |
| 2014/0220063 A1 | 8/2014 | Asari et al. |
| 2014/0220079 A1 | 8/2014 | Asari et al. |
| 2015/0010613 A1 | 1/2015 | Dubensky, Jr. et al. |
| 2018/0030137 A1 | 2/2018 | Van Eenennaam et al. |
| 2018/0030457 A1 | 2/2018 | Lauer et al. |
| 2021/0024940 A1 * | 1/2021 | Bishai ............... C12N 9/93 |

FOREIGN PATENT DOCUMENTS

| | | |
|---|---|---|
| CN | 105367617 | 3/2016 |
| CN | 106539814 | 3/2017 |
| CN | 106539816 | 3/2017 |
| CN | 106554416 | 4/2017 |
| WO | WO2018030457 | 6/2014 |
| WO | WO2013066264 | 5/2015 |
| WO | WO 2017019894 | 2/2017 |
| WO | WO2017075477 | 5/2017 |
| WO | WO2017106740 | 6/2017 |
| WO | WO2017185180 | 11/2017 |
| WO | WO2018009466 | 1/2018 |

OTHER PUBLICATIONS

Agarwa et al. 2009 (Cyclic AMP intoxication of macrophages by *Mycobacterium tuberculosis* adenylate cyclase; Nature Letters, 460: 98-104) (Year: 2009).*
Bai et al. 2012 (*Mycobacterium tuberculosis* Rv3586 (DacA) is a diadenylate cyclase that converts ATP or ADP into c-di-AMP; PLoS One 7(4): e35206) (Year: 2012).*
Ehrt et al. 2005 (Controlling gene expression in mycobacteria with anhydrotetracycline and Tet repressor; Nucleic Acids Research 33(2): e21) (Year: 2005).*
Abdul-Sater et al., "Cyclic-di-GMP and cyclic-di-AMP activate the NLRP3 inflammasome" EMBO Rep. 2013;14:900-6. PMID: 24008845.
Abdul-Sater et al., The overlapping host responses to bacterial cyclic dinucleotides. Microbes Infect 14, 188-197 (2012).
Agarwal et al., "Cyclic AMP intoxication of macrophages by a *Myoobaoterium tuberculosis* adenylate oyclase" Nature 460, 98-102 (2009).
Bai Y, et al., *Mycobacterium tuberculosis* Rv3586 (DacA) is a diadenylate cyclase that converts ATP or ADP into c-di-AMP PLoS One_ 2012;7:e35206. PMID: 22529992.

(Continued)

Primary Examiner — Mary Maille Lyons
(74) Attorney, Agent, or Firm — DLA Piper LLP (US)

(57) ABSTRACT

The present invention includes the discovery of a strain of *Mycobacterium* comprising an expression vector encoding a di-adenylate cyclase enzyme. The *Mycobacterium* is selected from the group consisting of *Mycobacterium tuberculosis, Mycobacterium bovis,* or a combination thereof and the preferred strain of *Mycobacterium* is BCG. The preferred expression vector is a mycobacterial expression vector including an hsp60 promoter and a DNA sequence of diadenylate cyclase (disA), or a functional part thereof. The strains of *Mycobacterium* are used in therapeutic applications including tuberculosis and cancer.

39 Claims, 23 Drawing Sheets

(56) References Cited

OTHER PUBLICATIONS

Barker et al., "STING-dependent recognition of cyclic di-AMP mediates type I interferon responses during Chlamydia trachomatis infection" MBio 4, e00018-00013 (2013).

Begnini et al., "Recombinant *Mycobacterium bovis* BCG for immunotherapy in nonmuscle invasive bladder cancer", Appl Microbiol Biotechnol (2015) 99.3741-3754.

Berry et al., "An interferon-inducible neutrophil-driven blood transcriptional signature in human tuberculosis" Nature 466, 973-977 (2010).

Burdette DL, et al., "STING is a direct innate immune sensor of cyclic di-GMP" Nature. 2011;478:515-8. PMID:21947006.

Cai et al., "The cGAS-cGAMPSTING Pathway of Cytosolic DNA Sensing and Signaling" Mol Cell 54, 289-296 (2014).

Campbell et al., "Vitamin D inhibits human immunodeficiency virus type 1 and *Mycobacterium tuberculosis* infection in macrophages through the induction of autophagy" PLoS Pathog 8, e1002689 (2012).

Shandra D, et al., "STING ligand c-di-GMP improves cancer vaccination against metastatic breast cancer" Cancer Immunol Res. 2014;2:901-10. PMID: 24913717.

Commichau FM, et al., "Making and Breaking of an Essential Poison: the Cyclases and Phosphodiesterases That Produce and Degrade the Essential Second Messenger Cyclic di-AMP in Bacteria" J Bacteriol. 2018;201: e00462-18. PMID: 30224435.

Collins et al., "Cyclic GMP-AMP Synthase Is an Innate Immune DNA Sensor for *Mycobacterium tuberculosis*" Cell Host Microbe. 2015;17:820-8.

Corrales L, et al., "Direct Activation of STING in the Tumor Microenvironment Leads to Potent and Systemic Tumor Regression and Immunity" Cell Rep. 2015;11:1018-30. PMID: 25959818.

Corrigan et al, "Cyclic di-AMP: another second messenger enters the fray" Nat Rev Microbic 11, 513-524 (2013).

Danilchanka et al., "Cyclic dinucleotides and the innate immune response" Cell. 2013;154:962-970. PMID: 23993090.

Deretic et al., "Autophagy in infection, inflammation and immunity" Nat Rev Immunol 13, 722-737 (2013).

Desvignes et al., "Dynamic roles of type I and type II IFNs in early infection with *Mycobacterium tuberculosis*" J Immunol 188, 6205-6215 (2012).

Dey et al., "A bacterial cyclic dinucleotide activates the cytosolic surveillance pathway and mediates innate resistance to tuberculosis" Nat Med. 2015;21:401-6.

Dey et al., "Crosstalk between *Mycobacterium tuberculosis* and the host cell" Semin Immunol 26, 486-496 (2014).

Dey et al., "Inhibition of Innate Immune Cytosolic Surveillance by a *Mycobacterium tuberculosis* Phosphodiesterase" Nature Chemical Biology 13:210-217 (2017).

Dhar et al., "Recombinant BCG approach for development of vaccines: cloning and expression of immunodominant antigens of M. tuberculosis", FEMS Microbiol Lett 2000, 190(2):309-16.

Diner EJ, et al., "The innate immune DNA sensor cGAS produces a noncanonical cyclic dinucleotide that activates human STING" Cell Rep. 2013;3:1355-61. PMID: 23707065.

Dorhoi et al., "Type I IFN signaling triggers immunopathology in tuberculosissusceptible mice by modulating lung phagocyte dynamics" Eur J Immunol (2014).

Dubensky TW Jr, et al., "Rationale, progress and development of vaccines utilizing STING-activating cyclic dinucleotide adjuvants" Ther Adv Vaccines. 2013;1:131-43. PMID: 24757520.

Ebensen T, et al., "Bis-(3',5')-cyclic dimeric adenosine monophosphate: strong Th1/Th2/Th17 promoting mucosal adjuvant" Vaccine. 2011;29:5210-20. PMID: 21619907.

Gao et al., "Cyclic GMP-AMP synthase is an innate immune sensor of HIV and other retroviruses" Science 341, 903-906 (2013).

Giacomini et al., "IFN-β improves BCG immunogenicity by acting on DC maturation", Journal of Leukocyte Biology, 2009, vol. 85, pp. 462-468.

Gutierrez et al., "Autophagy is a defense mechanism inhibiting BCG and *Mycobacterium tuberculosis* survival in infected macrophages" Cell 119, 753-766 (2004).

Houghten et al. (Vaccines, 1986, Edited by Fred Brown: Cold Spring Harbor Laboratory) (Year: 1986).

Ishikawa H, et al., "STING regulates intracellular DNA-mediated, type I interferon-dependent innate immunity" Nature. 2009;461:788-92. PMID: 19776740.

Jain et al., "Enhanced and enduring protection against tuberculosis by recombinant BCG-Ag85C and its association with modulation of cytokine profile in lung", PLoS One 2008, 3(12):e3869.

Jin L, et al., "MPYS is required for IFN response factor 3 activation and type I IFN production in the response of cultured phagocytes to bacterial second messengers cyclic-di-AMP and cyclic-di-GMP" J Immunol. 2011;187:2595-601. PMID: 21813776.

Karaolis DK, et al., "3',5'-Cyclic diguanylic acid (c-di-GMP) inhibits basal and growth factor-stimulated human colon cancer cell proliferation" Biochem Biophys Res Commun. 2005;329:40-5. PMID: 15721270.

Karaolis DK, et al., "Bacterial c-di-GMP is an immunostimulatory molecule" J Immunol. 2007;178:2171-81. PMID:17277122.

Kim et al., "Host cell autophagy activated by antibiotics is required for their effective antimycobacterial drug action" Cell Hlost Microbe 11, 457-468 (2012).

Kuchtey et al., "Enhancement of dendritic cell antigen cross-presentation by CpG DNA involves type I IFN and stabilization of class I MHC mRNA" J Immunol 175, 2244-2251 (2005).

Li et al., "Hydrolysis of 2'3'-cGAMP by ENPP1 and design of nonhydrolyzable analogs" Nat Chem Biol. 2014; 10:1043-8.

Manca et al., "Hypervirulent M. tuberculosis W/Beijing strains upregulate type I IFNs and increase expression of negative regulators of the Jak-Stat pathway" J Interferon Cytokine Res 25, 694-701 (2005).

Manca et al., "Virulence of a *Mycobacterium tuberculosis* clinical isolate in mice is determined by failure to induce Th1 type immunity and is associated with induction of IFN-alpha /beta" Proc Natl Acad Sc-i U S A 98, 5752-5757 (2001).

Manzanillo et al., "*Mycobacterium tuberculosis* activates the DNA-dependent cytosolic surveillance pathway within macrophages" Cell Host Microbe. 2012;11:469-80.

McWhirter et al., "A host type I interferon response is induced by cytosolic sensing of the bacterial second messenger cyclic-di-GMP" J Exp Med 206, 1899-1911 (2009).

Mehne FM, et al., "Control of the diadenylate cyclase CdaS in Bacillus subtilis: an autoinhibitory domain limits cyclic di-AMP production" J Biol Chem. 2014;289:21098-107. PMID: 24939848.

Nelson et al., "Riboswitches in eubacteria sense the second messenger c-di-AMP" Nat Chem Biol (2013).

O'Garra et al., "The immune response in tuberculosis" Annu Rev Immunol 31, 475-527 (2013).

Paludan et al., "Immune sensing of DNA" Immunity 38, 870-880 (2013).

Pandey et al., "NOD2, RIP2 and IRF5 play a critical role in the type I interferon response to *Mycobacterium tuberculosis*" PLoS Pathog 5, e1000500 (2009).

Parvatiyar et aL, "The helicase DDX41 recognizes the bacterial secondary messengers cyclic di-GMP and cyclic di-AMP to activate a type I interferon immune response" Nat Immunol 13, 1155-1161 (2012).

Platanias, "Mechanisms of type-I- and type-II-interferon-mediated signalling". Nat Rev Immunol 5, 375-386 (2005).

Romling, "Great times for small molecules: c-di-AMP, a second messenger candidate in Bacteria and Archaea" Sci Signal 1, pe39 (2008).

Rosenberg J, et al., "Structural and biochemical analysis of the essential diadenylate cyclase CdaA from Listeria monocytogenes" J Biol Chem_ 2015;290:6596-606. PMID: 25605729.

Schmeisser et al., "New function of type I IFN: induction of autophagy" J Interferon Cytokine Res 34, 71-78 (2014).

Schoggins et al., "Pan-viral specificity of IFN-induced genes reveals new roles for cGAS in innate immunity" Nature 505, 691-695 (2014).

(56) References Cited

OTHER PUBLICATIONS

Schwartz et al., "Hyperinduction of host beta interferon by a Listeria monocytogenes strain naturally overexpressing the multidrug efflux pump MdrT" Infect Immun 80, 1537-1545 (2012).

Skrnjug et al. "The Mucosal Adjuvant Cyclic di-AMP Exerts Immune Stimulatory Effects on Dendritic Cells and Macrophages" PLoS One 9, e95728 (2014).

Sun et al., "Cyclic GMP-AMP synthase is a cytosolic DNA sensor that activates the type I interferon pathway" Science 339, 786-791 (2013).

Takeuchi et al., "Pattern recognition receptors and inflammation" Cell 140, 805-820 (2010).

Thornley et al., "Type 1 IFN mediates cross-talk between innate and adaptive immunity that abrogates transplantation tolerance" J Immunol 179, 6620-6629 (2007).

Wassermann et al., "*Mycobacterium tuberculosis* Differentially Activates cGAS- and Inflammasome-Dependent Intracellular Immune Responses through ESX-1" Cell Host Microbe. 2015;17:799-810.

Watson et al., "Extracellular M. tuberculosis DNA targets bacteria for autophagy by activating the host DNA-sensing pathway" Cell 150, 803-815 (2012).

Watson et al., "The Cytosolic Sensor cGAS Detects *Mycobacterium tuberculosis* DNA to Induce Type I Interferons and Activate Autophagy" Cell Host Microbe. 2015;17:811-9.

Witte G, et al., "Structural biochemistry of a bacterial checkpoint protein reveals diadenylate cyclase activity regulated by DNA recombination intermediates" Mol Cell. 2008;30:167-78. PMID: 18439896.

Woodward JJ, et al., "c-di-AMP secreted by intracellular Listeria monocytogenes activates a host type I interferon response" Science. 2010;328:1703-5. PMID: 20508090.

Yang et al., "Deletion of the cyclic di-AMP phosphodiesterase gene (cnpB) in *Mycobacterium tuberculosis* leads to reduced virulence in a mouse model of infection", Mol Microbiol. 2014;93:65-79.

Zhang et al., "DarR, a TetR-like transcriptional factor, is a cyclic di-AMP-responsive repressor in *Mycobacterium smegmatis*" J Biol Chem 288, 3085-3096 (2013).

Zhang et al., "The helicase DDX41 senses intracellular DNA mediated by the adaptor STING in dendritic cells" Nat Immunol 12, 959-965 (2011).

Bai et al., "Cyclic AMP signalling in mycobacteria: redirecting the conversation with a common currency", Cellular Microbiology, Mar. 2011, 13(3): 349-358.

CA Office Action in Canadian Application No. 3,013,713, dated Feb. 9, 2022, 4 pages.

* cited by examiner

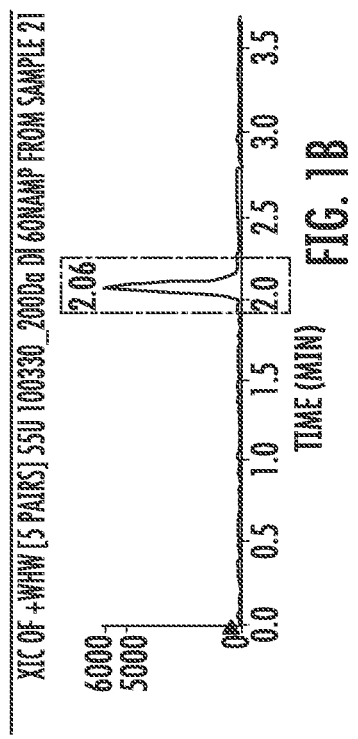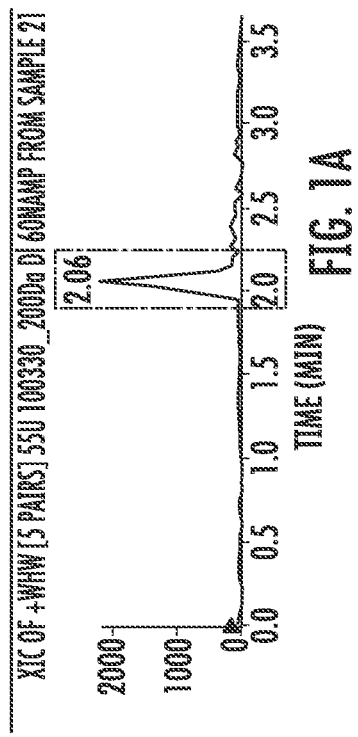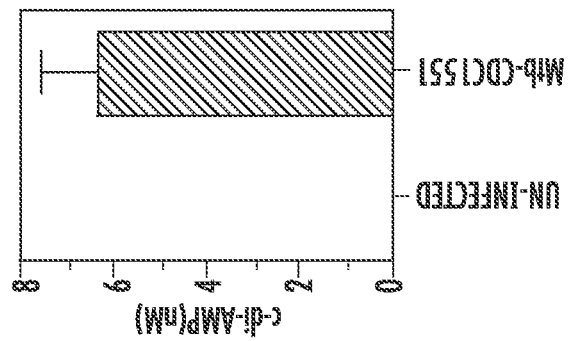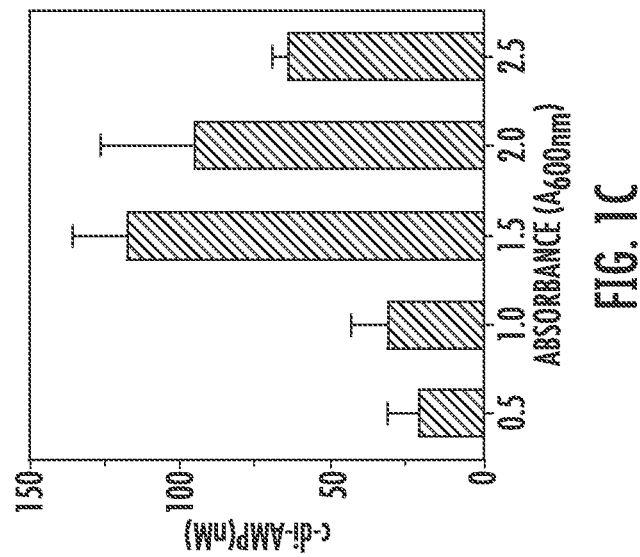

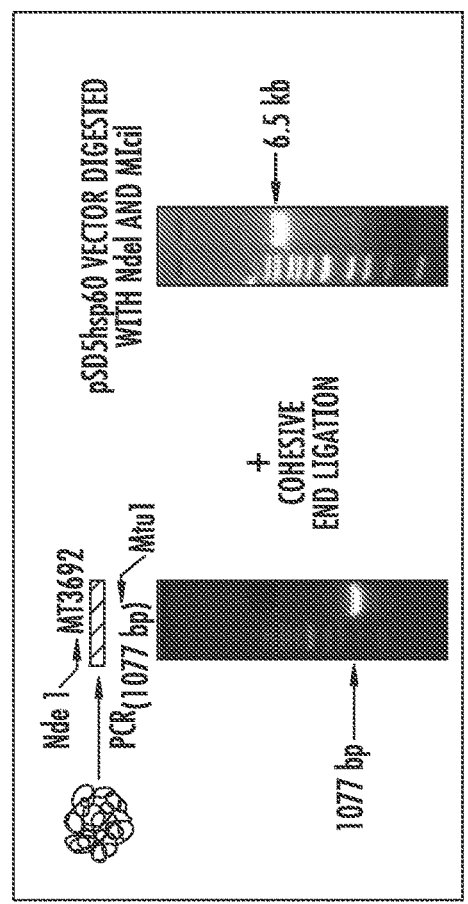
FIG. 2A
FIG. 2B
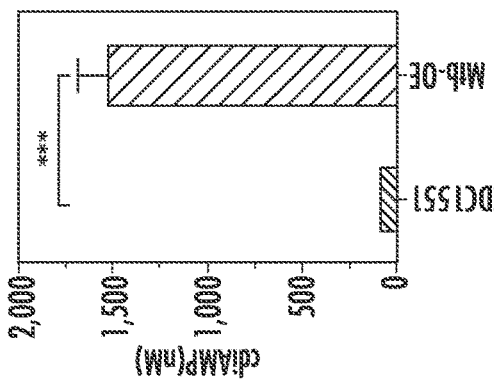
FIG. 2D
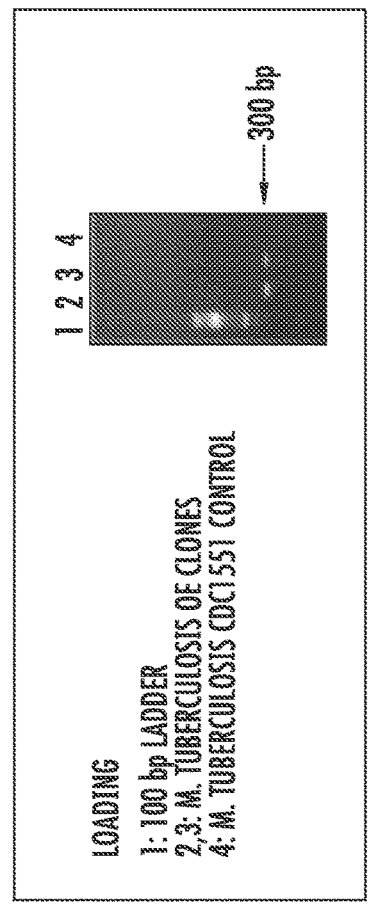
FIG. 2C

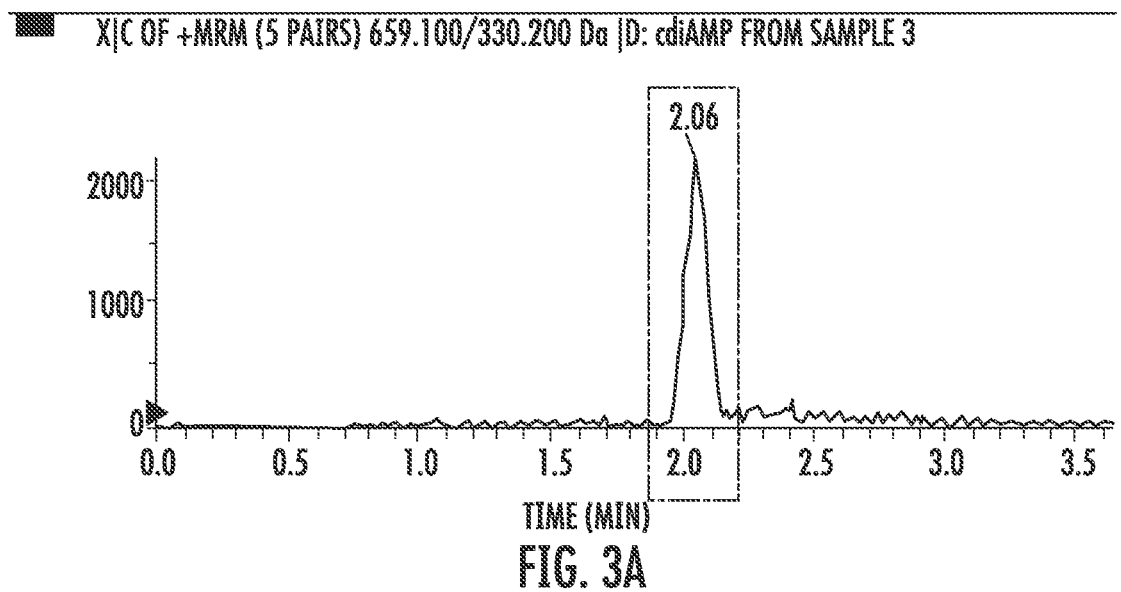
FIG. 3A
FIG. 3B
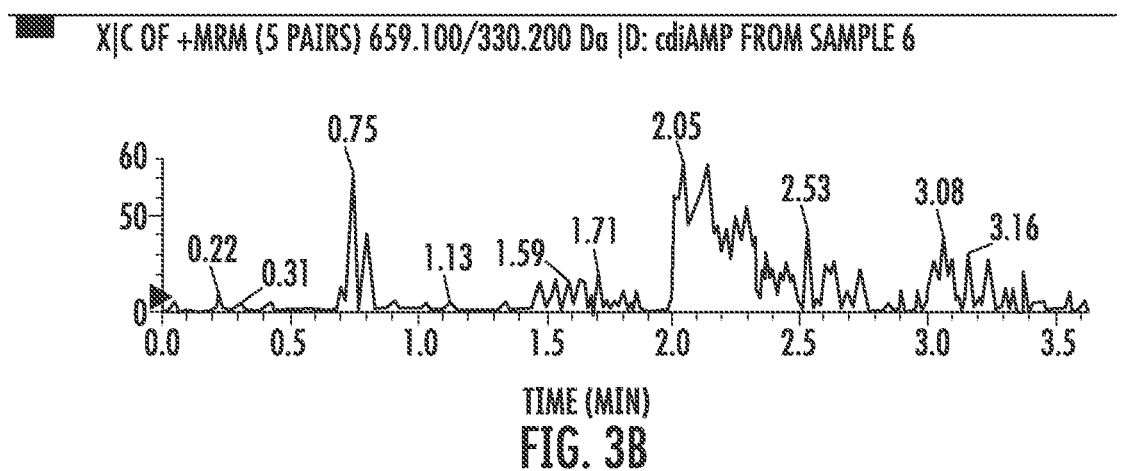
| SAMPLE NO. | SAMPLE NAME | SAMPLE TYPE | COMPONENT NAME | IS NAME | CONCENTRATION (nM) |
|---|---|---|---|---|---|
| 1 | Mtb-CDC1551 | CELL EXTRACT | c-di-AMP | cXMP | 1.27E+02 |
| 2 | Mtb-CDC1551 | CELL EXTRACT | c-di-AMP | cXMP | 1.29E+02 |
| 3 | Mtb-disA-KO | CELL EXTRACT | c-di-AMP | cXMP | UNDETECTABLE |
| 4 | Mtb-disA-KO | CELL EXTRACT | c-di-AMP | cXMP | UNDETECTABLE |
FIG. 3C

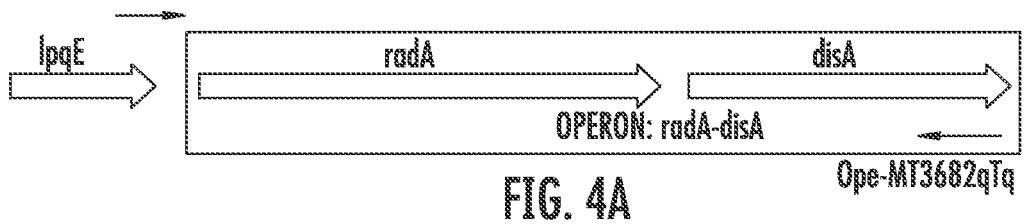
FIG. 4A
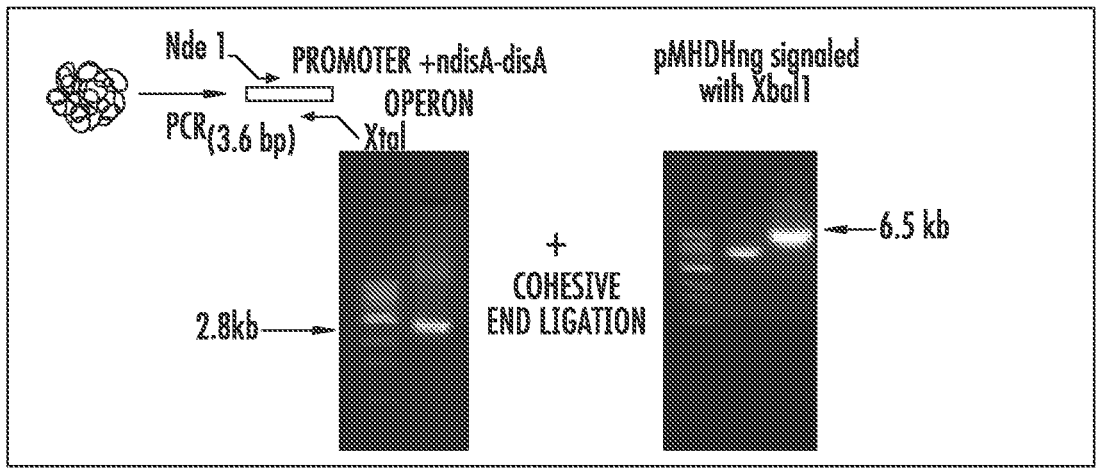
FIG. 4B
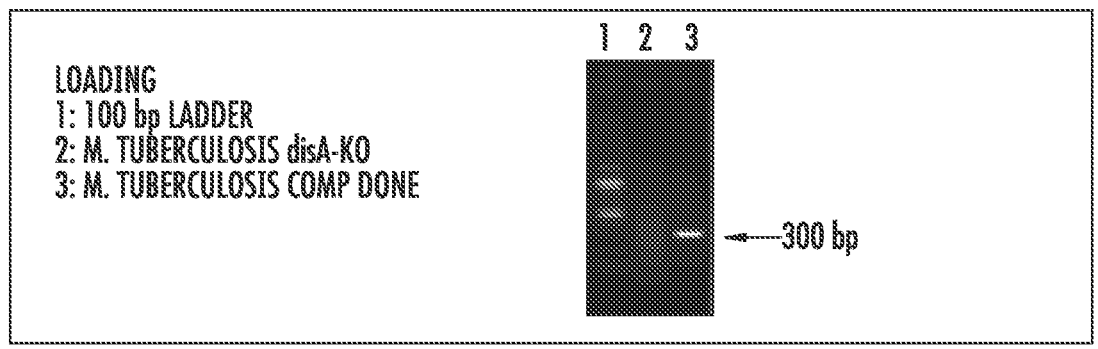
FIG. 4C
| SAMPLE NO. | SAMPLE NAME | SAMPLE TYPE | COMPONENT NAME | IS NAME | CONCENTRATION (nM) |
|---|---|---|---|---|---|
| 1 | Mtb-disA-KO | CELL EXTRACT | c-d-AMP | cXMP | UNDETECTABLE |
| 2 | Mtb-disA-KO | CELL EXTRACT | c-d-AMP | cXMP | UNDETECTABLE |
| 3 | Mtb-COMP | CELL EXTRACT | c-d-AMP | cXMP | 1.27E+03 |
| 4 | Mtb-COMP | CELL EXTRACT | c-d-AMP | cXMP | 1.58E+03 |
FIG. 4D

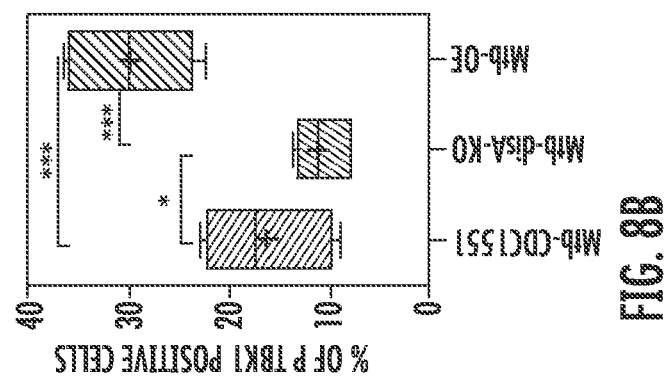
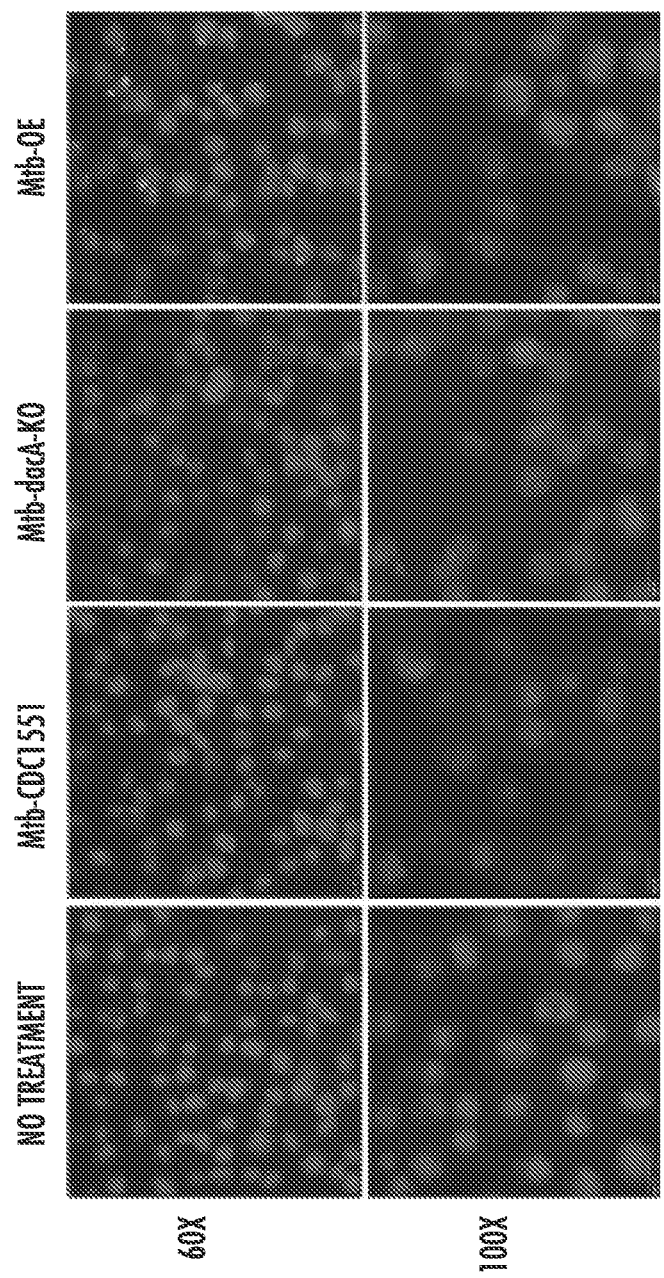
FIG. 8A
FIG. 8B

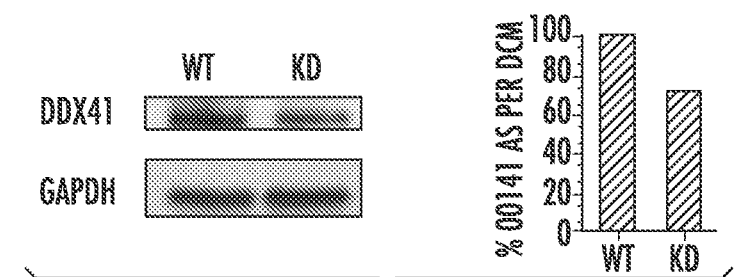
FIG. 9A
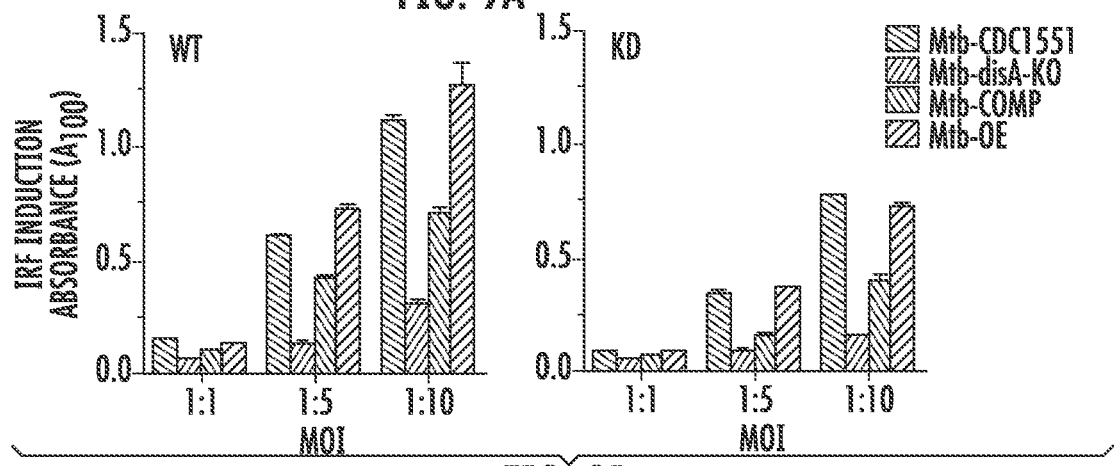
FIG. 9B
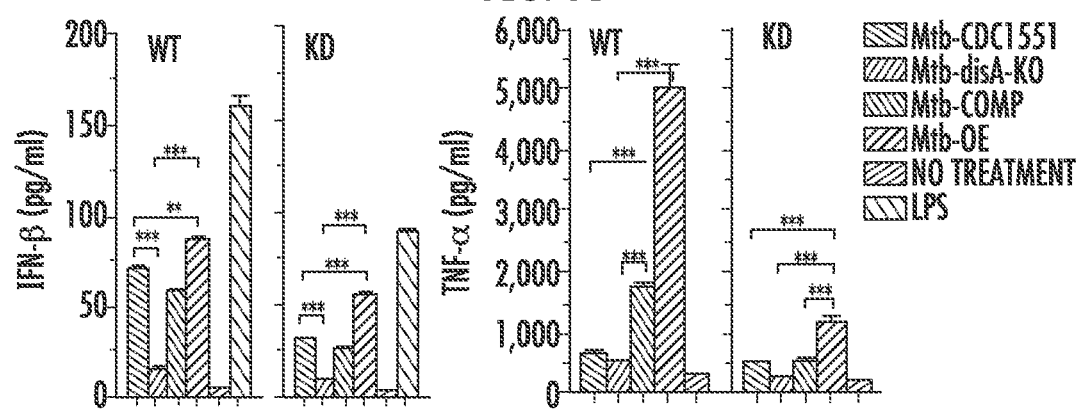
FIG. 9C
FIG. 9D

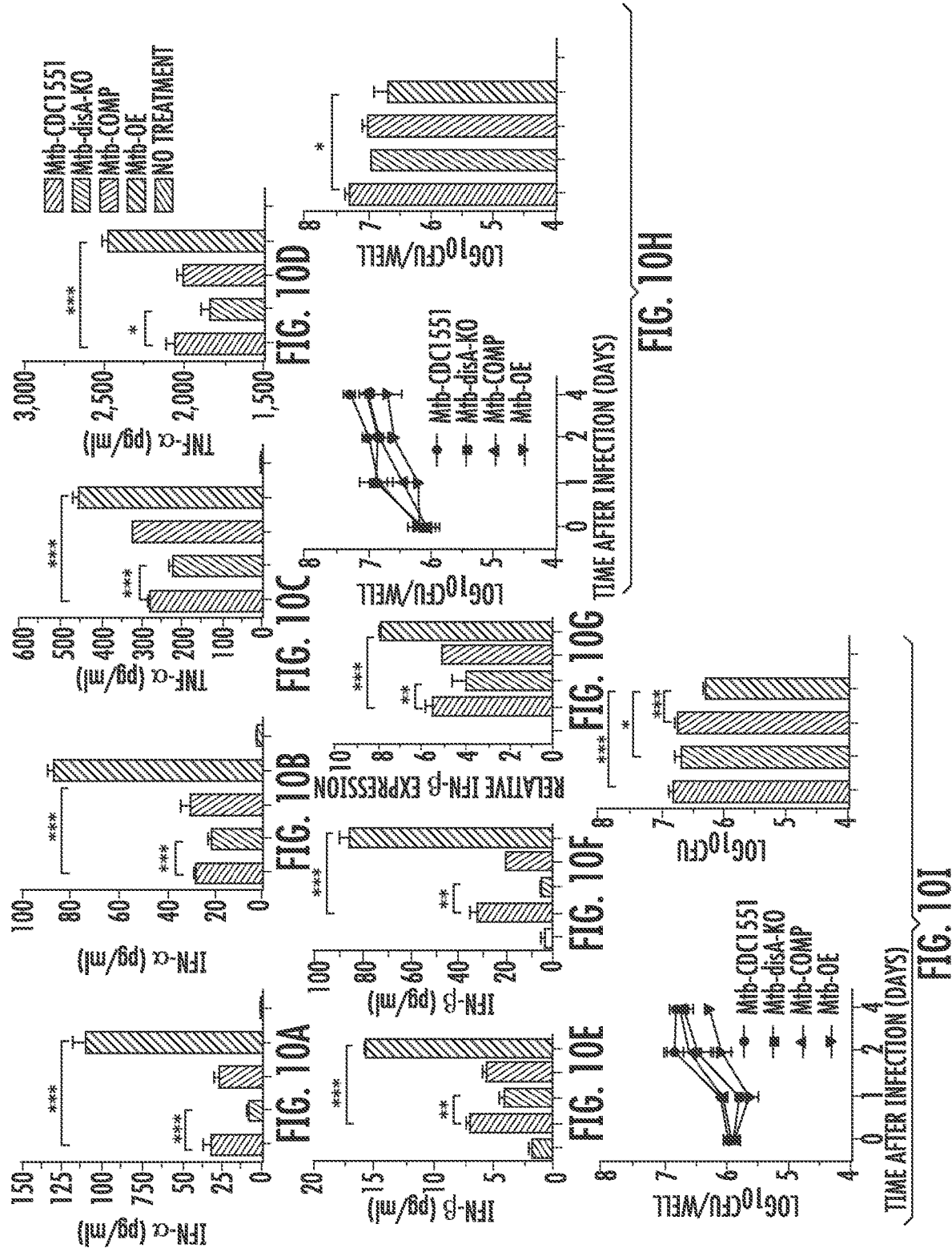

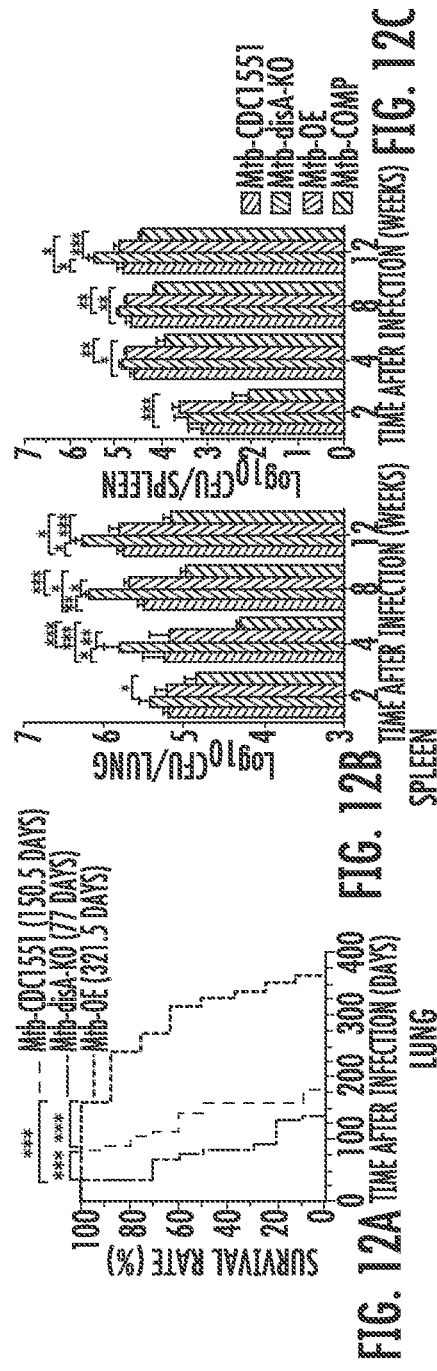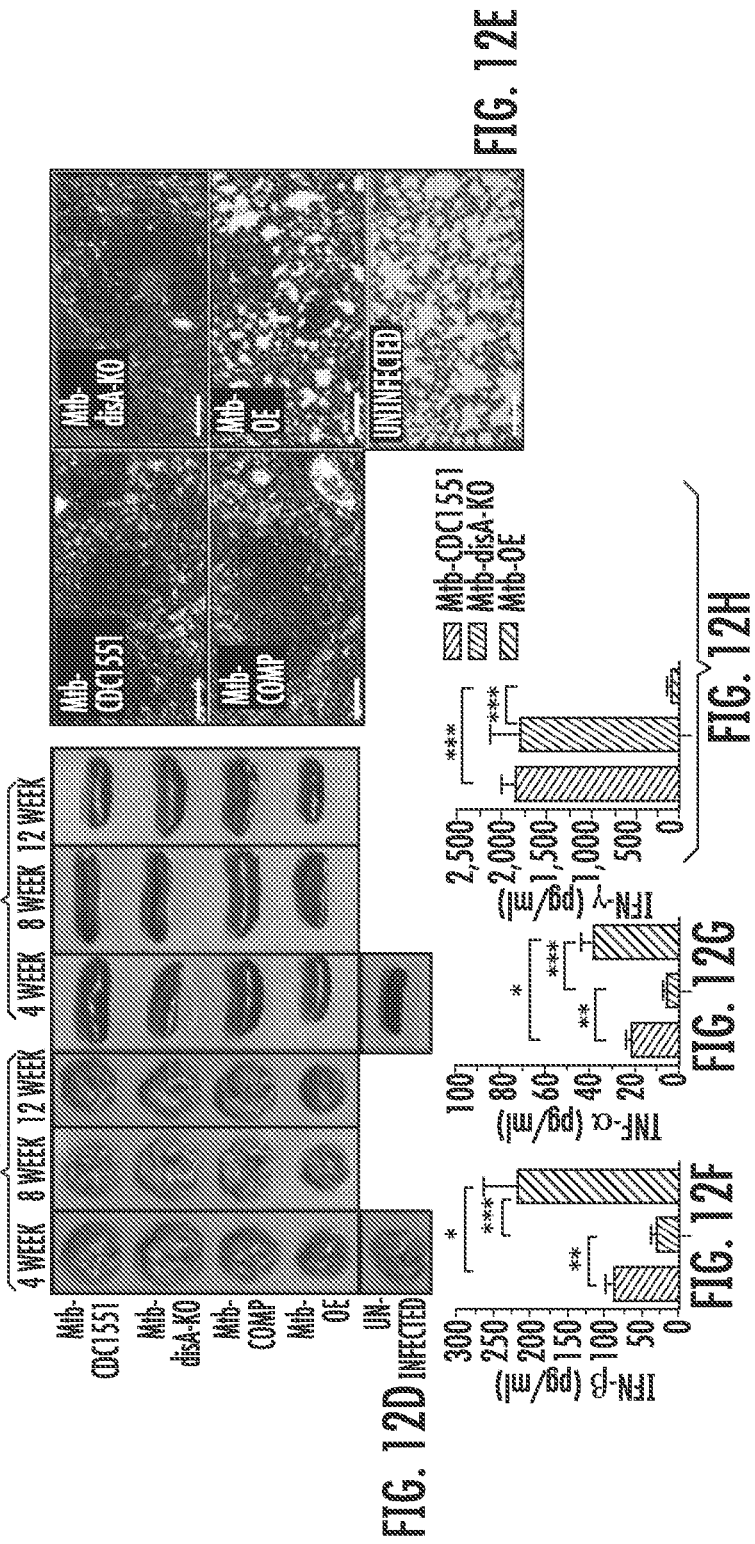

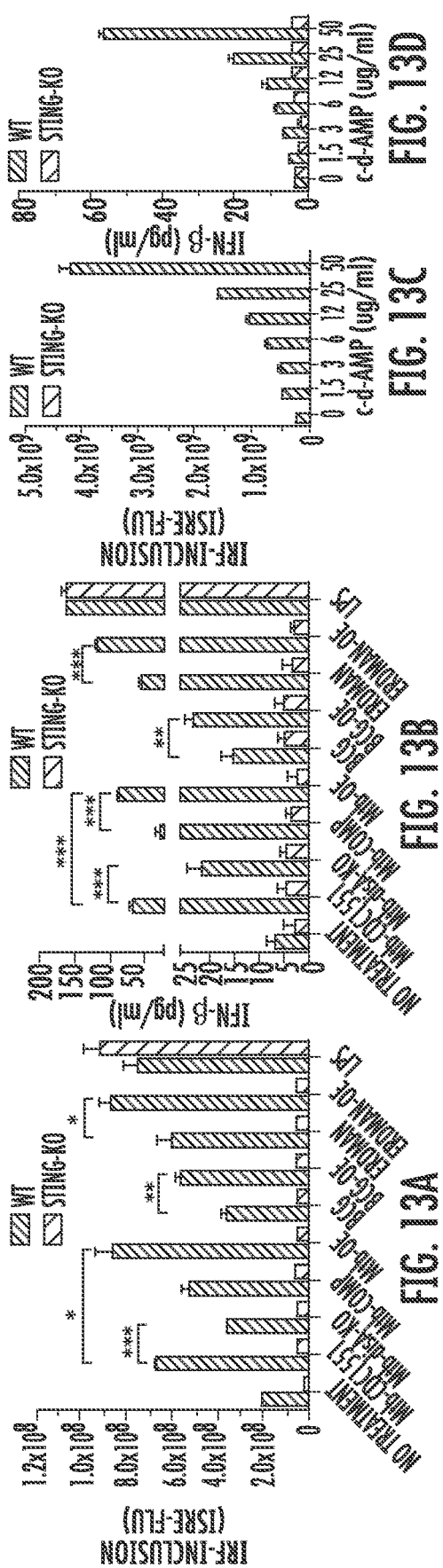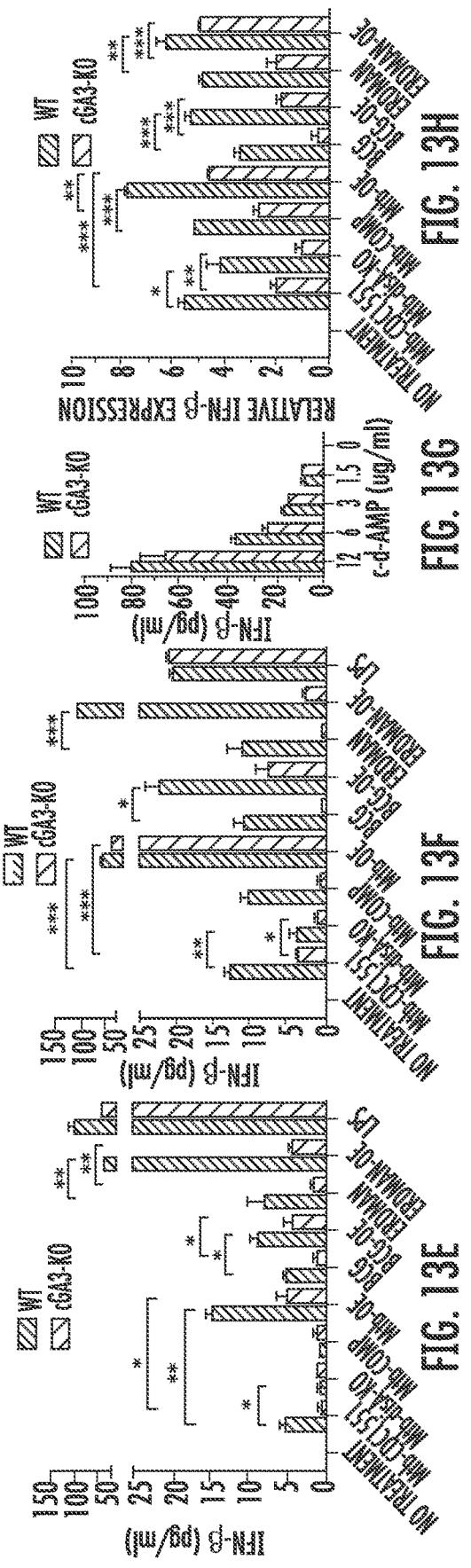

| NAME | DESCRIPTION |
|---|---|
| PLASMIDS | |
| pSD5.hsp60 | MYCOBACTERIAL EXPRESSION PLASMID WITH hsp60 PROMOTER |
| pMH94Hyg | INTEGRATIVE MYCOBACTERIAL EXPRESSION PLASMID WITHOUT PROMOTER |
| pSD5hsp60.MT3692 | disA OVER-EXPRESSION PLASMID |
| pMH94Hyg.MT3692 | PLASMID USED FOR COMPLEMENTATION OF Mtb-disA-KO |
| M. TUBERCULOSIS STRAINS | |
| Mtb-CDC1551 | WILD TYPE M. TUBERCULOSIS |
| Mtb-disA-KO | M. TUBERCULOSIS TRANSPOSON MUTANT FOR disA GENE (MT3692) |
| Mtb-COMP | disA COMPLEMENTED Mtb-disA-KO STRAIN |
| Mtb-OE | M. TUBERCULOSIS CDC1551 STRAIN OVER EXPRESSING disA (MT3692) |
| ERDMAN | WILD TYPE M. TUBERCULOSIS ERDMAN STRAIN |
| ERDMAN-OE | M. TUBERCULOSIS ERDMAN STRAIN OVER EXPRESSING disA (MT3692) |
| M. BOVIS BCG STRAINS | |
| BCG | M. BOVIS BCG PASTEUR |
| BCG-OE | BCG STRAIN OVER EXPRESSING disA (MT3692) |

FIG. 14

MICE EXPERIMENT

| GROUPS | IMMUNIZATION (-42 DAY) | PRE-INFECTION-IMM.ASSAY (DAY-1) | INFECTION (DAY 0) | CFU DAY 1 | CFU/IMM. ASSAY WEEK 10 | CFU/IMM. ASSAY WEEK 18 |
|---|---|---|---|---|---|---|
| SALINE | 25 | 6 | 19 | 3 | 4 | 4 |
| BCG | 25 | 6 | 19 | 3 | 4 | 4 |
| rBCG-disA | 25 | 6 | 19 | 3 | 4 | 4 |
| TOTAL | 75 | 18 | 57 | 9 | 12 | 12 |

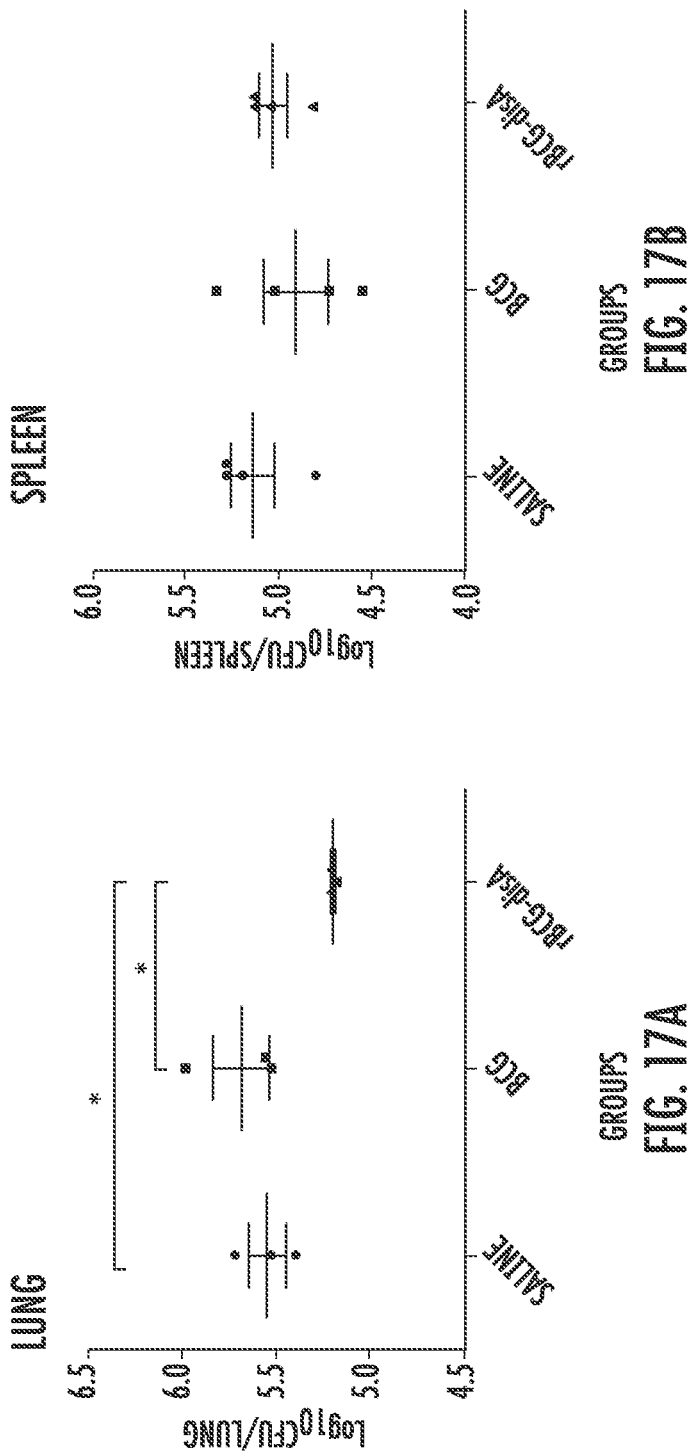

GUINEA PIG EXPERIMENT

| GROUPS | IMMUNIZATION (-42 DAY) | INFECTION (DAY 0) | CFU DAY 1 | CFU/HISTO/ IMM. ASSAY WEEK 14 | CFU/HISTO/ IMM. ASSAY WEEK 18 |
|---|---|---|---|---|---|
| SALINE | 15 | 12 | 1 | 5 | 6 |
| BCG | 15 | 12 | 1 | 5 | 6 |
| rBCG-docA | 15 | 12 | 1 | 5 | 6 |
| TOTAL | 45 | 36 | 3 | 15 | 18 |

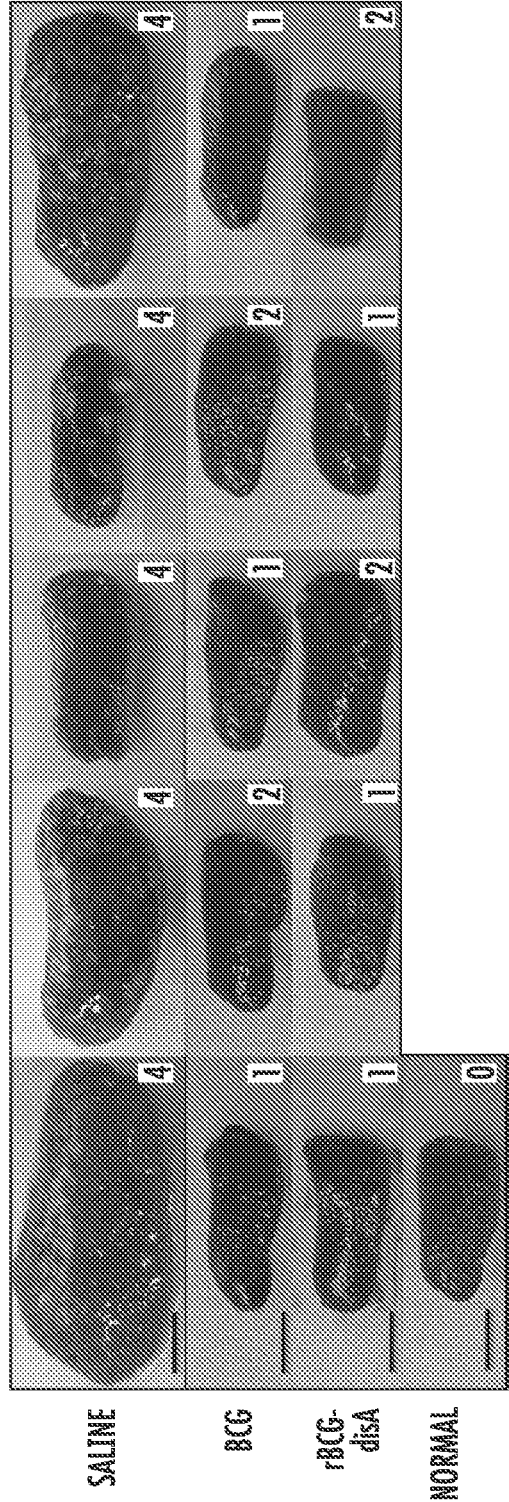
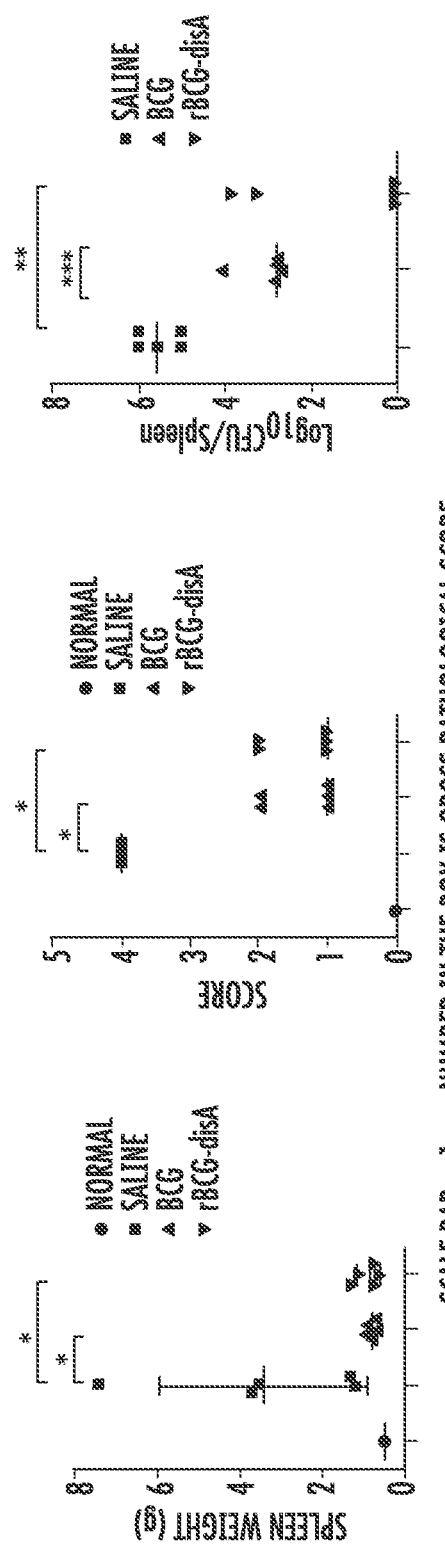
SCALE BAR = 1 cm, NUMBER IN THE BOX IS GROSS PATHOLOGICAL SCORE.
FIG. 20

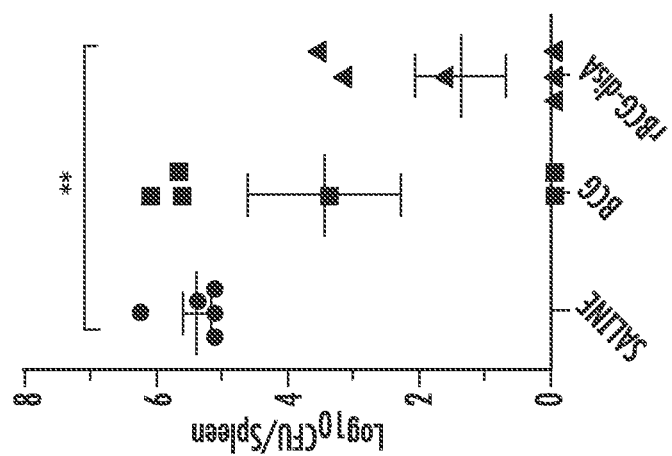
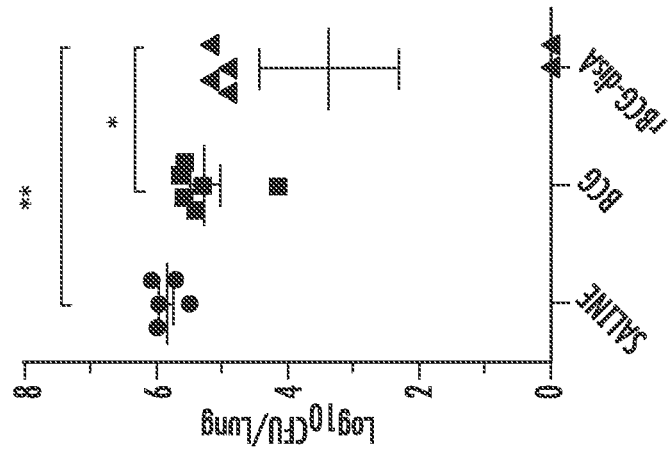
FIG. 23

METHODS OF TREATING CANCER USING BACTERIA EXPRESSING C-DI-AMP

CROSS-REFERENCE TO RELATED APPLICATIONS

This application is a divisional application of U.S. application Ser. No. 16/147,916, filed Oct. 1, 2018, which is a divisional application of U.S. application Ser. No. 15/550,434, filed Aug. 11, 2017, now issued as U.S. Pat. No. 10,130,663, which is a 371 application of International Patent Application No. PCT/US2016/017248, filed Feb. 10, 2016 which claims benefit under 35 USC § 119(e) to U.S. Provisional Application 62/114,610, filed Feb. 11, 2015. The disclosure of each of the prior applications is considered part of and is hereby incorporated by reference in the disclosure of this application.

STATEMENT OF GOVERNMENTAL INTEREST

This invention was made with government support under grant nos. AI036973, AI037856, AI097138 from the National Institutes of Health. The government has certain rights in the invention.

INCORPORATION-BY-REFERENCE

All references, including publications, patent applications, and patents, cited herein are hereby incorporated by reference to the same extent as if each reference were individually and specifically indicated to be incorporated by reference and were set forth in its entirety herein.

BACKGROUND OF THE INVENTION

Nucleotides are indispensable components of all living cells, as they make up DNA and RNA, and serve as important energy sources. Nucleotides also have key roles in signaling in eukaryotic, bacterial and archaeal cells. In bacteria, signaling nucleotides such as cyclic AMP and guanosine tetra- or pentaphosphate ((p)ppGpp) have been classically linked to carbon metabolism and the stringent response, which is caused by nutrient limitation. However, it has become clear that signaling nucleotides contribute to the regulation of multiple different pathways; for example, in addition to its involvement in central carbon metabolism, cAMP is also involved in the regulation of both biofilm formation and virulence gene expression in many pathogenic bacteria. One of the latest signaling nucleotides to be identified is cyclic di-AMP (c-di-AMP), which is the second cyclic dinucleotide shown to be produced by bacteria, after cyclic di-GMP (c-di-CiMP). It has been suggested that c-di-AMP and c-di-GMP regulate very different processes.

c-di-AMP is produced from two molecules of ATP by diadenylyl cyclase (DAC) enzymes and is degraded to pApA by phosphodiesterase (PDE) enzymes. The dinucleotide was initially discovered during a structural study on *Thermatoga maritinta* DNA integrity scanning protein (DisA), which is a homologue of *Bacillus subtilis* DisA (formerly known as YacK), a bacterial DNA damage checkpoint protein that can delay sporulation in the event of DNA damage. The first report of c-di-AMP production by bacterial cells came in 2010, when the dinucleotide was identified as a molecule secreted into the cytosol of host cells by the intracellular bacterial pathogen *Listeria monocytogenes*. Since then, c-di-AMP has been detected in cellular extracts from *Streptococcus pyogenes*, *B. subtilis*, *Chlamylia trachomatis* and *Staphylococcus aureus*, and a DisA-type c-di-AMP-synthesizing enzyme from *Mycobacterium tubercaosis* has been characterized biochemically.

Although most of the mechanistic details still await molecular characterization, the regulation of cellular pathways by c-di-AMP presumably follows the same general principles as for the other signaling nucleotides. Environmental changes are sensed either directly or indirectly by the nucleotide-synthesizing or nucleotide-degrading enzymes, leading to a change in the cellular nucleotide concentration. At high concentrations, c-di-AMP is expected to bind to a specific set of receptor or target proteins and allosterical by alter their function or the function of downstream effector proteins, thus controlling specific cellular pathways. Although many details of the c-di-AMP signaling network remain to be discovered, this nucleotide has been linked to the regulation of fatty acid synthesis in *Mycobacterium smegmatis*, to the growth of *S. aureus* in low-potassium conditions, to the sensing of DNA integrity in *B. subtilis* and to cell wall homeostasis in multiple species.

The *M. tuberculosis* genome encodes a di-adenylate cyclase enzyme (disA, also called dacA; encoded by gene Rv3586 (also called MT3692) in the H37Rv genome or MT3692 in the CDC1551 genome) that synthesizes c-di-AMP from ATP or ADP4. Orthologs of disA exist in all mycobacterial genomes with the exception of *M. leprae*. However, the role of c-di-AMP in *M. tuberculosis* physiology and mechanism of its interaction with the host immune system is poorly understood. However, the existing model for *M. tuberculosis* infection is that extracellular mycobacterial DNA is the only ligand for CSP activation within macrophages, which leads to increased autophagy and bacterial clearance in an ESX-1 secretion system-dependent manner, excluding any role for bacterial CDNs in CSP activation.

The mammalian innate immune system is composed of receptors that collectively serve as a pathogen sensor to monitor the extracellular, vacuolar, and cytosolic cellular compartments. Recognition of microbes within these distinct compartments leads to cellular responses that are commensurate with the microbial threat. Although both pathogenic and nonpathogenic microbes interact with extracellular and vacuolar compartments, infectious disease agents often mediate their pathogenesis by directly entering the cytosol or through delivery of virulence factors into the host cell cytosolic compartment. Thus, the innate immune system may distinguish between pathogenic and nonpathogenic microbes by monitoring the cytosol.

Several distinct pathways of innate immunity are present in the host cell cytosol. One, termed the cytosolic surveillance pathway (CSP), detects bacterial, viral, and protozoan pathogens, leading to the activation of interferon regulatory factor 3 (IRF3) and nuclear factor kappalight-chain-enhancer of activated B cells (NF-κB), resulting in the induction of interferon-β (IFN-β) and co-regulated genes. Some ligands that activate this pathway are known, for example, viral and bacterial nucleic acids. However, the ligands and host receptors that lead to IFN-β production after exposure to nonviral microbes—including *L. monocytogenes, M. tuberculosis, F. tularensis, L. pneumophila, B. abortis*, and *T. cruzi*—remain unknown. The mechanisms and role of c-di-AMP signaling in *Mycobacterium tuberculosis* infection must be identified and treatments that prevent, alleviate, or cure tuberculosis must be developed.

Bacille Calmette Guerin (BCG) is the most widely used vaccination in the world. BCG is made of a live, weakened strain of *Mycobacterium bovis*, (a cousin of *Mycobacterium* tuberculosis, the TB bacteria). It was developed in the 1930's and it remains the only vaccination available against tuberculosis today. Despite its protection against active TB in children, BCG has failed to protect adults against TB infection and active disease development, especially in developing countries where the disease is endemic. Some of key reasons for failure of BCG is low immunogenicity and its inability to induce maturation of DC efficiently. Among various strategies that have been employed so far to improve the protective potential of BCG involve construction of rBCG, which could confer similar or higher protection along with induction of a better immunological memory than BCG. Most of the methodologies used to achieve greater immunogenicity involve (i) over-expression of promising immuno-dominant antigens either singularly or as fusion with other immuno-dominant antigens, (ii) over-expression and reintroduction of antigens lost during the attenuation process or (iii) over-expression of mammalian cytokines in BCG such as IL-2, IL-12, IL-15, and GM-CSF. New methods of tuberculosis vaccination are needed to prevent the spread of disease.

In addition, more than 60,000 new cases of bladder cancer are diagnosed each year the United States accounting for approximately 13,000 deaths. BCG-based therapy is currently the most effective intravesical therapy for nonmuscle invasive bladder cancer (NMIBC) and it represents the only agent known to reduce the progression of invasive bladder cancer into muscle. It is widely accepted that an intact immune system is a prerequisite to a successful therapy. BCG-induced antitumor effects depend on a sequence of events involving a complex interplay of soluble and cellular immune mediators and a cross-talk between innate and adaptive immunity. Limitations of BCG therapy include recurrence of the disease after initiation of BCG therapy. Consequently, new BCG strains enhancing the prevention or cure, and minimizing the recurrence rate, of cancer in patients must be identified.

SUMMARY OF THE INVENTION

One embodiment of the invention is a pharmaceutical composition comprising a compound, salt, solvate, or stereoisomer of a synthetic c-di-AMP, and a pharmaceutically acceptable carrier. This pharmaceutical composition may include at least one or more other compounds enhancing immunogenicity such as mycobacterial DNA, IFN, or c-di-AMP and combinations thereof.

Another embodiment of the invention is a method of treating a bacterial infection in a subject comprising administering to the subject an effective amount of a compound, salt, solvate, or stereoisomer of synthetic c-di-AMP.

Another embodiment of the invention is a method of treating tuberculosis (TB) in a subject comprising administering an effective amount of a compound, salt, solvate, or stereoisomer of c-di-AMP.

Another embodiment of the invention is the discovery of one or more strain(s) of *Mycobacterium* comprising an expression vector encoding a di-adenylate cyclase enzyme. The *Mycobacterium* is preferably selected from the group consisting of *Mycobacterium tuberculosis, Mycobacterium bovis*, or a combination thereof. The preferred strain of *Mycobacterium bovis* is a *Mycobacterium bovis* bacille Calmette-Guérin strain ("BCG") that preferably over-expresses a diadenylate cyclase (disA) of *M. tuberculosis* (Rv3586) from a mycobacterial expression vector (or plasmid). The most preferred strains are BCG-pSDhsp60.MT3692 (a BCG strain harboring the episomal plasmid pSDhsp60.MT3692), and BCG-pMH94Hyg.MT3692 (a BCG strain harboring the integrative plasmid pMH94Hyg.MT3692). Many strains of BCG maybe transformed with plasmids of the present invention, pSDhsp60.MT3692 and pMH94Hyg.MT3692 to form novel pharmaceutical compositions. The preferred mycobacterial expression vector includes an hsp60 promoter and a DNA sequence of diadenylate cyclase (disA), or a functional part thereof, wherein the expression of di-adenylate cyclase enzyme or a functional part thereof is regulated by the hsp60 promoter. The term "functional part thereof" means a part of the diadenylate cyclase enzyme that maintains its enzymatic activity. The one or more strains of *Mycobacterium* described above are used in therapeutic applications including tuberculosis and cancer, specifically nonmuscle invasive bladder cancer.

Another embodiment of the invention is a pharmaceutical composition of the one or more strain(s) of *Mycobacterium* described above and a pharmaceutically acceptable carrier. This pharmaceutical composition may be combined with at least one or more compounds enhancing immunogenicity described above.

Another embodiment of the invention is a method of vaccinating a subject against TB comprising administering to the subject and effective amount of the one or more strain(s) of *Mycobacterium* described above and a pharmaceutically acceptable carrier. This method of vaccination may also include one or more compounds enhancing immunogenicity described above.

Another embodiment of the invention is a method of treating or preventing cancer in a subject comprising administering to the subject an effective amount of the one or more strain(s) of *Mycobacterium* described above and a pharmaceutically acceptable carrier. This method of treating or preventing cancer may also include one or more compounds enhancing immunogenicity described above.

BRIEF DESCRIPTION OF THE DRAWINGS

FIGS. 1A-1D illustrates the c-di-AMP production by *M. tuberculosis* in the in vitro broth culture.

FIGS. 2A-2D illustrates generation and confirmation of *M. tuberculosis* over expression.

FIGS. 3A-3C illustrates transposon insertion mutant of *Mycobacterium tuberculosis* CDC 1551 for MT3692 gene is unable to produce c-di-AMP.

FIGS. 4A-4D illustrates generation and confirmation of *M tuberculosis*-CDC 1551 MT3692 complemented strain (Mtb-COMP)

FIGS. 8A-8B illustrates increased phosphorylation of TBK1 in macrophage following infection with the Mtb-OE strain.

FIGS. 9A-9D illustrates knock down of DDX41 in macrophage leads to reduced induction of type I IFN and TNF-α response.

FIGS. 10A-10I illustrates modulation of host cytokine response and intracellular growth of *M. tuberculosis* by c-di-AMP. (a) Levels of IFN-β in culture media at 24 h post-infection from resting and (b) IFN-β/LPS activated J774.1 cells infected with various Mtb-strains at an MOI of 1:20. (c) Levels of TNF-α in culture media at indicated time points from resting and (d) IFN-β/LPS activated J774.1 cells infected with various Mtb-strains at an MOI of 1:20. (e) Levels of IFN-β in culture media at 24 h post-infection from BMDM and (f) BMDC cells infected with various Mtb-strains at an MOI of 1:10. ELISA Data are mean±SE of at the least three experiments (n=3). *, p<0.05; , p<0.01 and *, p<0.001 by One-way ANOVA with Tukey's post test. (g) IFN-β mRNA were assessed by qRT-PCR in BMDCs infected with various Mtb-strains at 24 h post-infection; data are mean±SD (n=3) and representative of two experiments. , p<0.01 and *, p<0.001 by One-way ANOVA with Tukey's post test. (h) Growth kinetics of various Mtb-strains in resting and (i) IFN-☐/LPS activated J774.1 cells. Data are Mean CFUs±SD at each time point (n=3) and representative of two experiments. Bar diagrams (right panels in h and i) represent Mean CFUs±SD at Day 4. *, p<0.05 and ***, p<0.001 by Student's t-test (2-tailed).

FIGS. 12A-12H illustrates attenuation of virulence and pathogenicity in c-di-AMP over-producing *M. tuberculosis* strain. (a) Survival of mice (n=10) following infection with various Mtb-strains. ***, p<0.001 by Log-rank (Mantel-Cox) test. (b) Growth kinetics of various *M. tuberculosis*-strains in mouse lungs and (c) spleen after aerosol infection. Data are mean±SE (n=4). *, p<0.05; , p<0.01 and *, p<0.001 by Two-way ANOVA with Bonferroni post-test. (d) Gross and (e) histo-pathological features of lungs and spleen of mouse infected with various *M. tuberculosis*-strains. Scale bar is 100 μm. (f) Levels of IFN-β, (g) TNF-α and (h) IFN-β in the serum of mice infected with *M. tuberculosis*-strains possessing varied ability to produce c-di-AMP. Data are mean±SE (n=4). *, p<0.05; , p<0.01 and *, p<0.001 by Student's t-test (2-tailed).

FIGS. 13A-13H illustrates contribution of STING and cytosolic DNA receptor cGAS to c-di-AMP mediated activation of IFN-β during *M. tuberculosis* infection. (a, c) IRF pathway activation as measured by luciferase reporter assay and (b, d) IFN-β levels in the 18 h post-infection (MOI=1:5) and post-stimulation culture supernatants of mouse RAW264.7 derived STING ablated [STING-KO] and control [WT] macrophage IRF reporter cells. (e) IFN-β induction in BMDMs and (f) BMDCs from control [WT] and cGAS ablated [cGAS-KO] mouse following infection (MOI=1:10) with various *Mycobacterium* strains. (g) c-di-AMP concentration dependent induction of IFN-β in mouse BMDMs. Data are mean±SE of at the least three experiments (n=4 in a, b; n=3 in c, d, e, f, g).*, p<0.05; , p<0.01 and *, p<0.001 by Student's t-test (2-tailed). (h) Levels of IFN-β mRNA were determined by real-time RT-PCR in BMDCs derived from wild type cGAS sufficient [WT] and cGAS ablated [cGAS-KO] mouse following infection (MOI=1:10) with various *Mycobacterium* strains. The IFN-β mRNA expression levels were normalized to-actin expression and are represented relative to those of untreated cells. Data are mean±SD (n=3) and is representative of two experiments. *, p<0.05; , p<0.01 and *, p<0.001 by Student's t-test (2-tailed).

FIG. 14 illustrates plasmids and *Mycobacterium* used in the invention.

FIGS. 17A-17B illustrates a) lung and b) spleen CFU 18 weeks post infection from mice described in FIG. 15.

FIG. 20 illustrates the gross pathology and CFU of spleen 14 weeks post-infection of the guinea pigs described in FIG. 18.

FIG. 23 illustrates the graphs of lung and spleen infection of the guinea pigs described in FIG. 18.

DETAILED DESCRIPTION OF THE INVENTION

As shown in FIG. 1, *M. tuberculosis* produced and secreted c-di-AMP. The amount of c-di-AMP was quantified in a 7H9 broth culture and within the bacteria (intracellular). Intracellular c-di-AMP levels were observed to increase during late-log and stationary phases of growth of *M. tuberculosis* compared to early log phase growth. After 24 hours of infection of J774 mouse macrophage cells with *M. tuberculosis*, the c-di-AMP produced by the bacteria was detected in the macrophage cytosol of the J774 cells.

Strains of *M. tuberculosis*, producing different amounts of c-di-AMP, were formed and then used in studies of the present invention. As illustrated in FIG. 2, a recombinant *M. tuberculosis* strain Mtb-OE (OE means "over expression" of c-di-AMP) was formed having over 95-fold expression of an endogenous di-adenylate cyclase gene, disA, and a resultant increase in the production of c-di-AMP by 20 fold when compared to the *M. tuberculosis* CDC1551 a wild type (WT) strain of *M. tuberculosis*. As described in SUPP FIG. 3, a recombinant *M. tuberculosis* strain Mtb-disA-KO (KO means "Knock Out" of the disA gene) was produced with a transposon insertion disrupting the di-adenylate cyclase domain of disA making the strain substantially free of c-di-AMP. c-di-AMP is produced by a single di-adenylate cyclase in *M. tuberculosis* so knocking out this gene knocks further knocks out c-di-AMP production. As shown in FIG. 4, a strain Mtb-COMP was formed by taking the Mtb-disA-KO strain and transforming it with an expression vector with an endogenous disA gene and native promoter. The addition of the expression vector reconstituted c-di-AMP production in Mtb-disA-KO.

Figure 5:
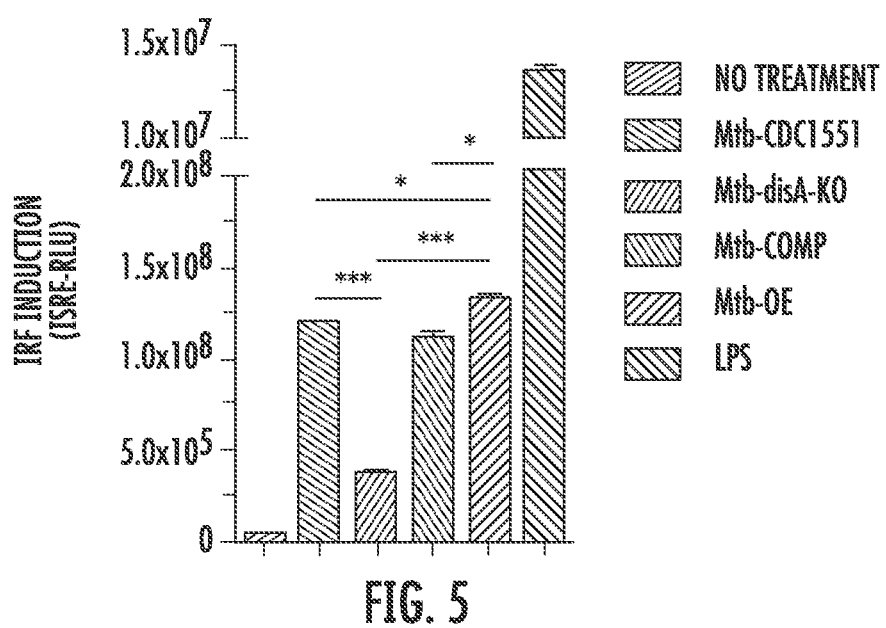
FIG. 5 illustrates Interferon Regulatory Factor (IRF) pathway activation following infection with various *M. tuberculosis* strains with varied levels of c-di-AMP production.
Figure 6A:
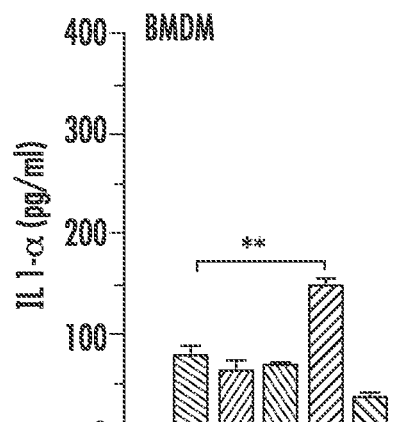
FIGS. 6A-6F illustrates increased induction of pro-inflammatory cytokines following infection with the c-di-AMP over-expressing *M. tuberculosis* strain.
Figure 6B:
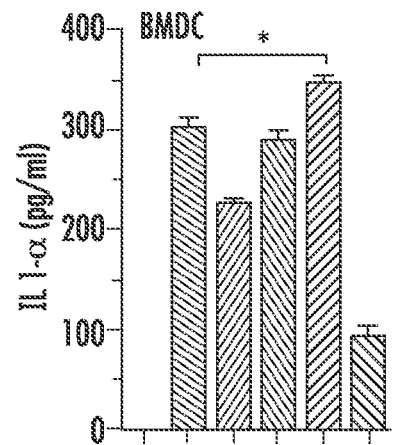
Figure 6C:
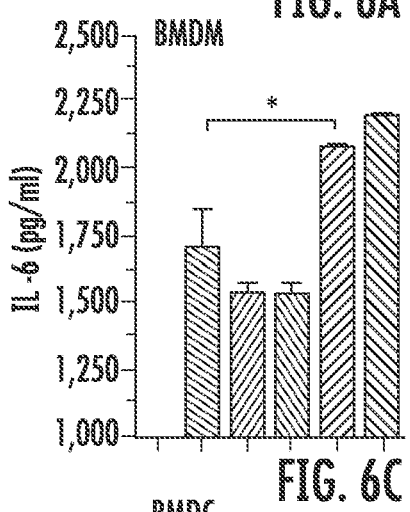
Figure 6D:
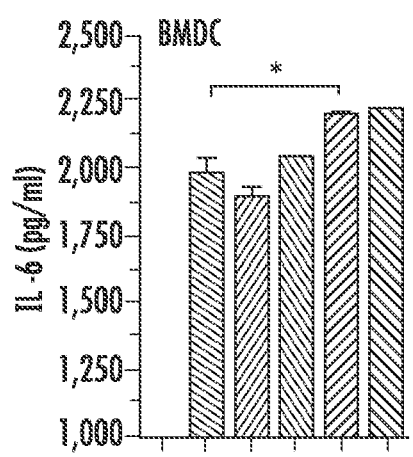
Figure 6E:
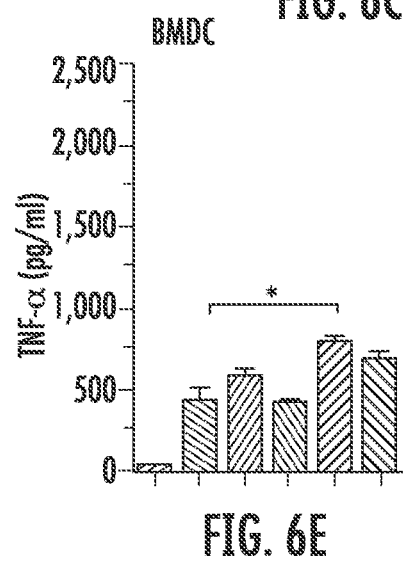
Figure 6F:
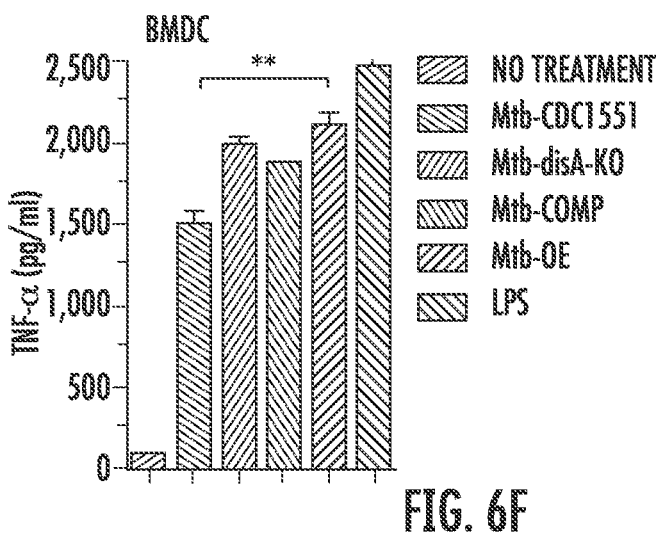

As shown in FIG. 10, J774.1 mouse macrophage cells were infected with these *M. tuberculosis* strains (Mtb-CDC1551, Mtb-disA-KO, Mtb-COMP, and Mtb-OE) expressing different amounts of c-di-AMP in vitro. After different incubation times, the amount of IFN-β produced by the J774.1 cells were measured. As shown in FIG. 10, infection with the Mtb-disA-KO strain resulted in a significant reduction in IFN-β induction by J774.1 cells compared to infection with the Mtb-CDC1551. Conversely, infection with the Mtb-OE strain resulted in an enhanced induction of IFN-β by both resting and activated J774.1 cells. Notably, Mtb-OE infected cells also secreted significantly higher levels of TNF-α compared to the Mtb-WT infected cells (or Mtb-CDC1551), whereas Mtb-disA-KO infected cells produced lower TNF-α levels compared to other groups (FIG. 10c, d). As shown in SUPP FIG. 5, the patterns of Interferon Regulatory Factor (IRF) pathway activation in THP1-human monocyte cells was analyzed and IFN-β responses in mouse primary bone marrow derived macrophages (BMDM) and dendritic cells (BMDC) (FIG. 10e, f) were comparable. However, the mouse BMDCs are a comparatively better IFN-β producer than BMDMs in response to *M. tuberculosis* infection. Induction of IFN-β was further confirmed by real time RT-PCR of the BMDC cells infected with the various *M. tuberculosis* strains (FIG. 10g). We also observed induction of significantly higher levels of pro-inflammatory cytokines including IL-1α, IL-6 and TNF-α by both BMDMs and BMDCs following infection with the c-di-AMP over-expressing *M. tuberculosis* strain Mtb-OE (FIG. 6). These observations suggest that perturbation of c-di-AMP levels in *M. tuberculosis* not only influences the CSP mediated Type I IFN response but also plays a critical role in modulating the pro-inflammatory cytokine signature of the infected cells.

Figure 7:
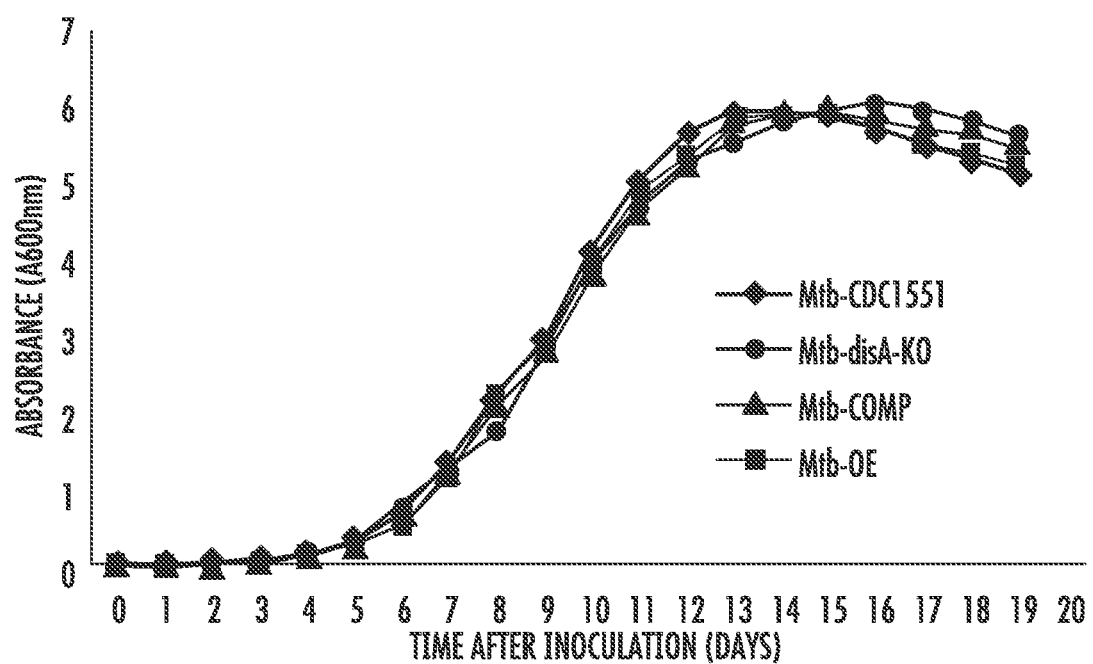
FIG. 7 illustrates in vitro growth pattern of *M. tuberculosis* strains possessing different c-di-AMP production levels.

Taking into account the ambiguous role of the Type I IFN response in host control of TB, the growth patterns of these *M. tuberculosis* strains in resting and IFN-β/LPS activated J774.1 cells were monitored. While all *M. tuberculosis* WT and recombinant strains exhibited identical growth rates in 7H9 broth culture (FIG. 7), the Mtb-OE strain over expressing c-di-AMP exhibited significantly diminished intracellular growth compared with the other *M. tuberculosis* strains (FIG. 10h, i). Growth attenuation of the knock out strain Mtb-disA-KO which is c-di-AMP deficient strain was not noticed. These observations reveal that over-expression of c-di-AMP by *M. tuberculosis* results in significant attenuation of the intracellular growth of the Mtb-OE strain.

Figure 11A:
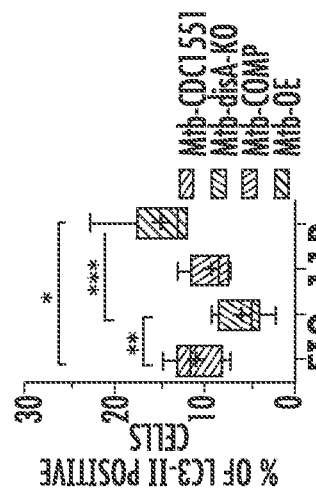
FIGS. 11A-11C illustrates c-di-AMP produced by *M. tuberculosis* induces autophagy in macrophage cells. (a) Fluorescence confocal images of J774.1 cells, fixed after 6 hr of infection with various *M. tuberculosis* strains and stained with anti-LC3 antibody; Nuclei-Blue (DAPI), LC3b-Green (AF488). Scale bars depicts 20 μm for 40× images and 10 μm for 100× images. (b) Quantitative analysis of LC3 positive J774.1 cells showing puncta formation. Only those cells were considered as positive and included for quantification, which exhibited formation of large LC3 aggregates occupying area >1 μm, Percentage of LC3-II positive cells were calculated and data are depicted by box plot indicating Mean (+), Median (−) with quartiles (box margins) and ranges (bars) (n=9). *, p<0.05; , p<0.01 and *, p<0.001 by One-way ANOVA with Tukey's post test. (c) Western blot analysis of LC3-I and LC3-II and GAPDH (loading control) of J774.1 cells at 6 hr after infection along with bar diagram depicting densitometric ratios of normalized LC3-II/LC3-I levels. Data are mean±SD (n=2) from two experiments.*, p<0.05 by Student's t-test (2-tailed).
Figure 11B:
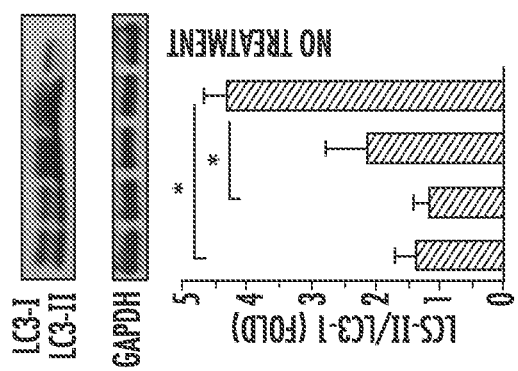
Figure 11C:
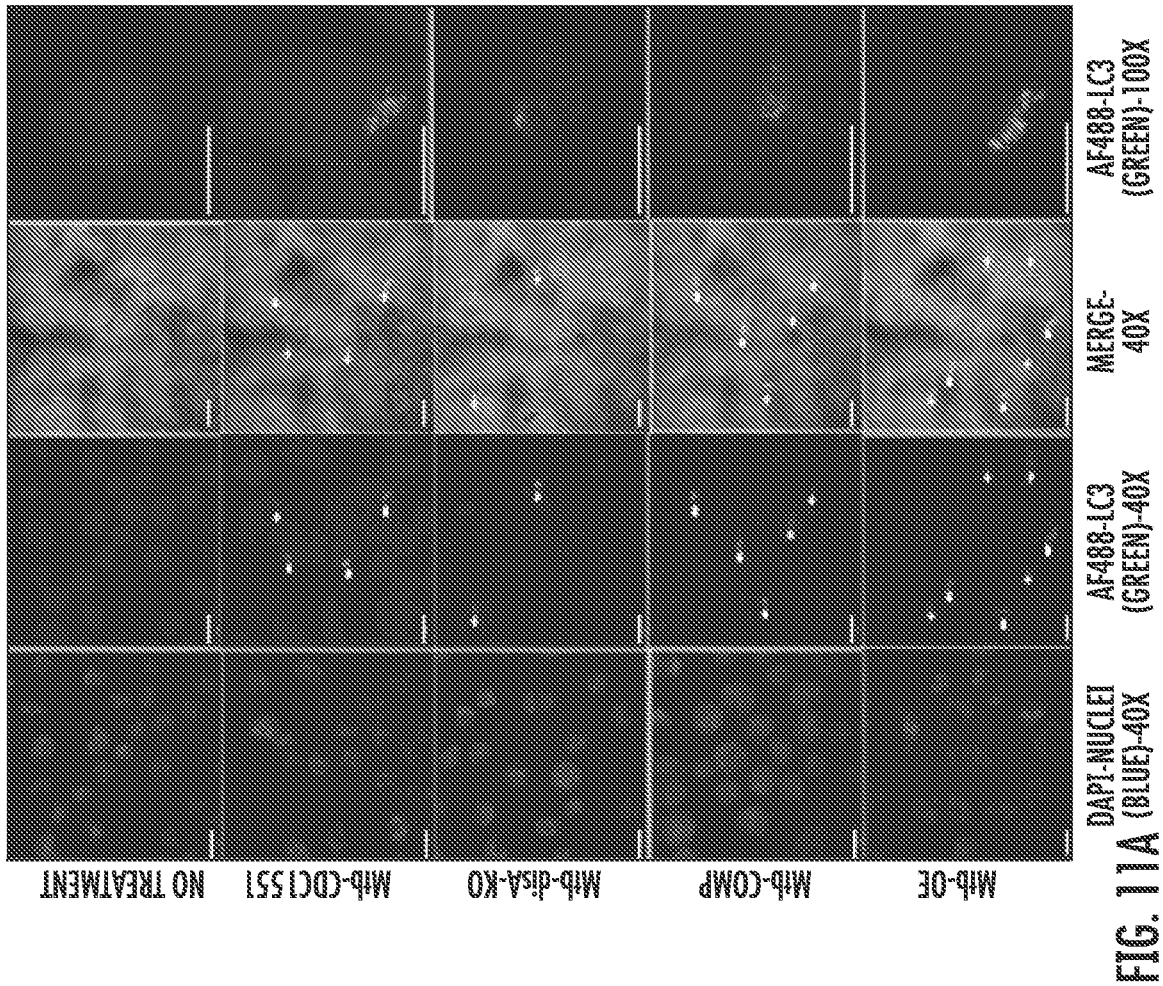
Figures 15A, 15B:
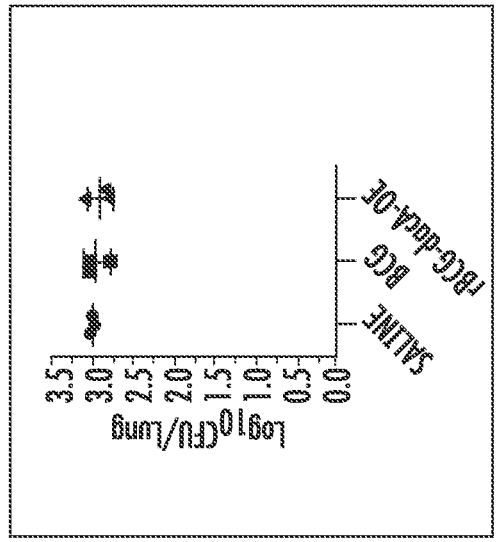
FIGS. 15A-15B illustrates a) Mice experiments with a strain of BGC including an expression vector encoding a diadenylate cyclase protein (rBCG-disA) and b) Graph of CFU one day post infection.
Figure 16:
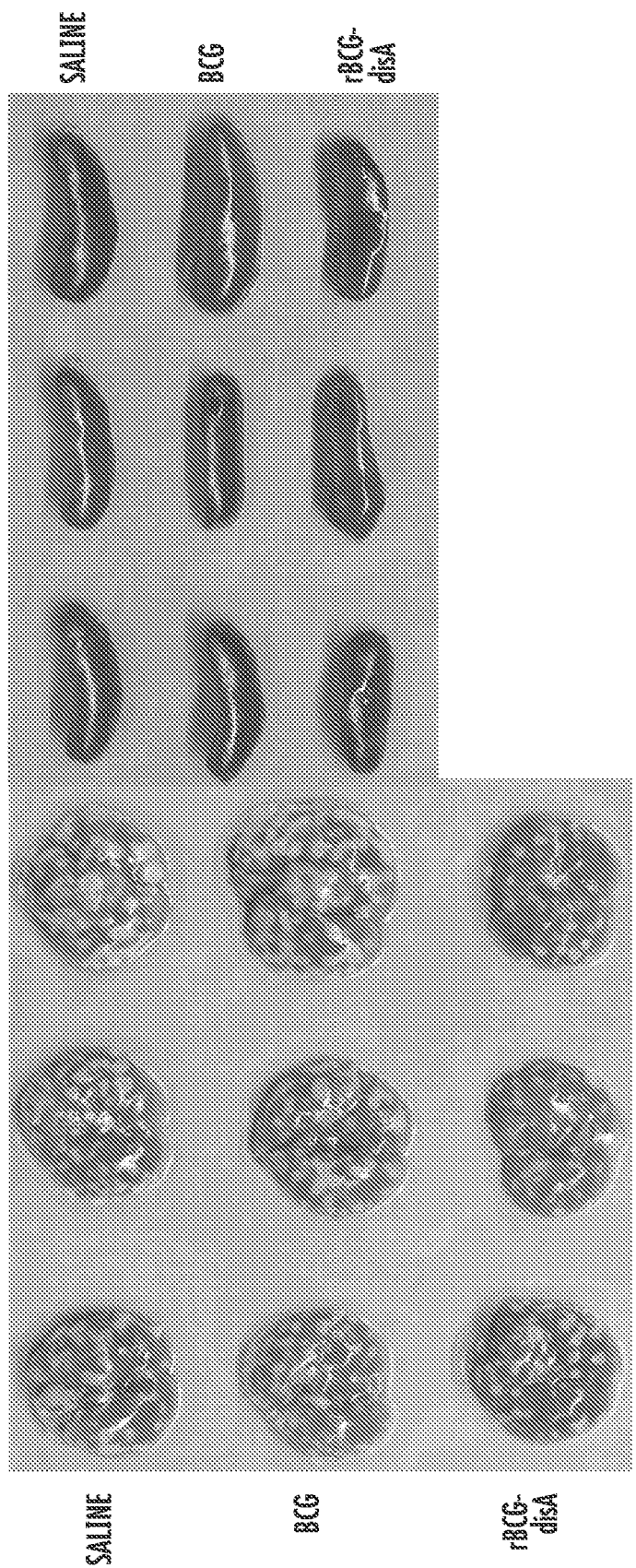
FIG. 16 illustrates the gross pathology of organs 18 weeks post infection from mice described in FIG. 15.
Figures 18A, 18B:
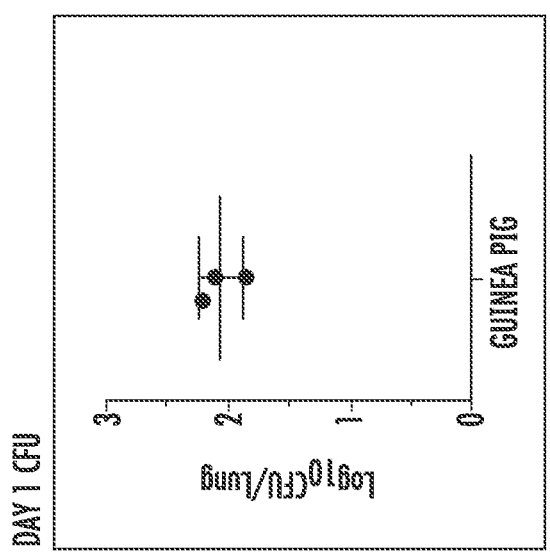
FIGS. 18A-18B illustrates the a) prophylactic potential of BCG strain including a DNA expression vector encoding disA (rBCA-disA) in guinea pigs and b) CFU one day post infection.
Figure 19:
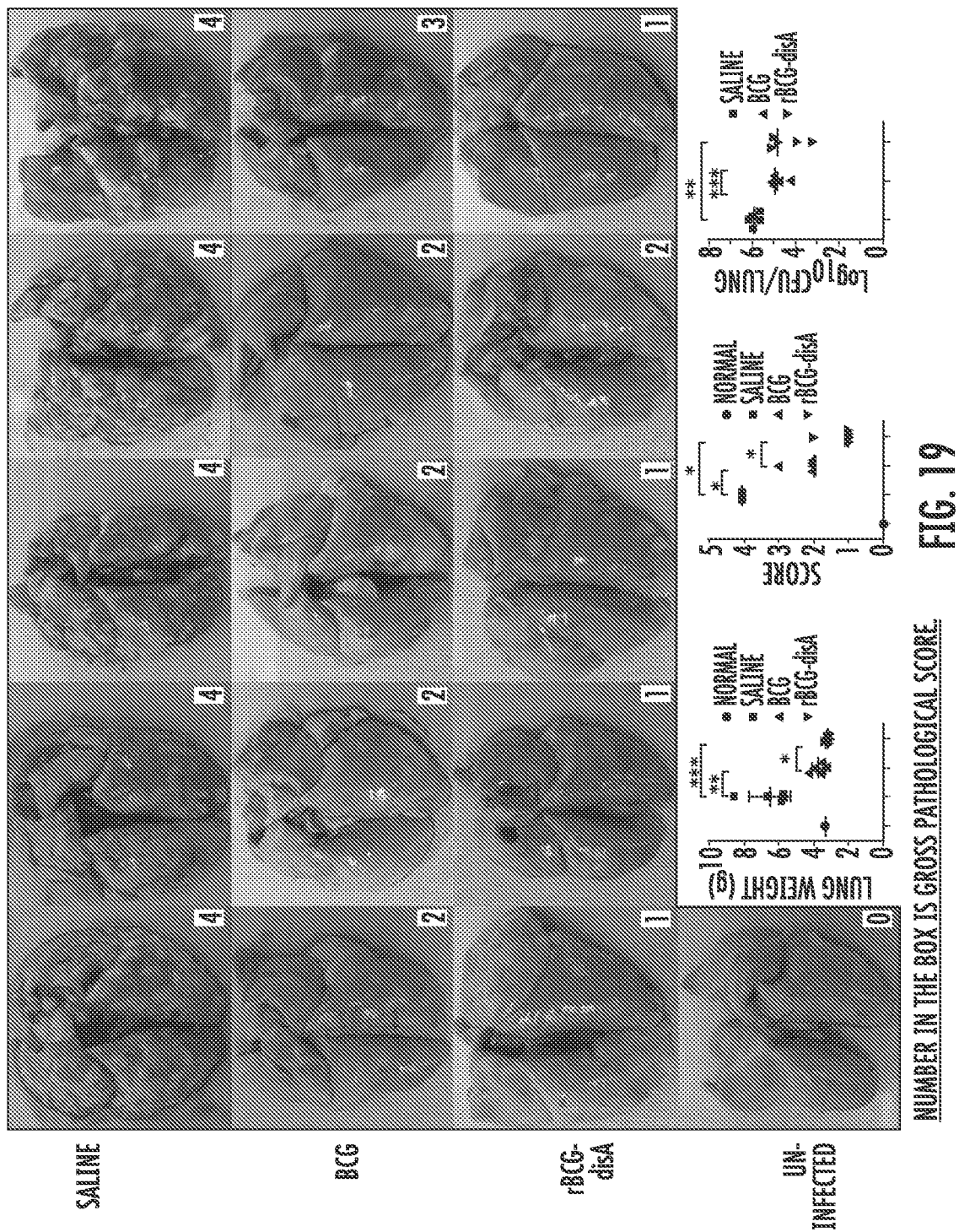
FIG. 19 illustrates the gross pathology and CFU of lungs 14 weeks post-infection of the guinea pigs described in FIG. 18.
Figure 21:
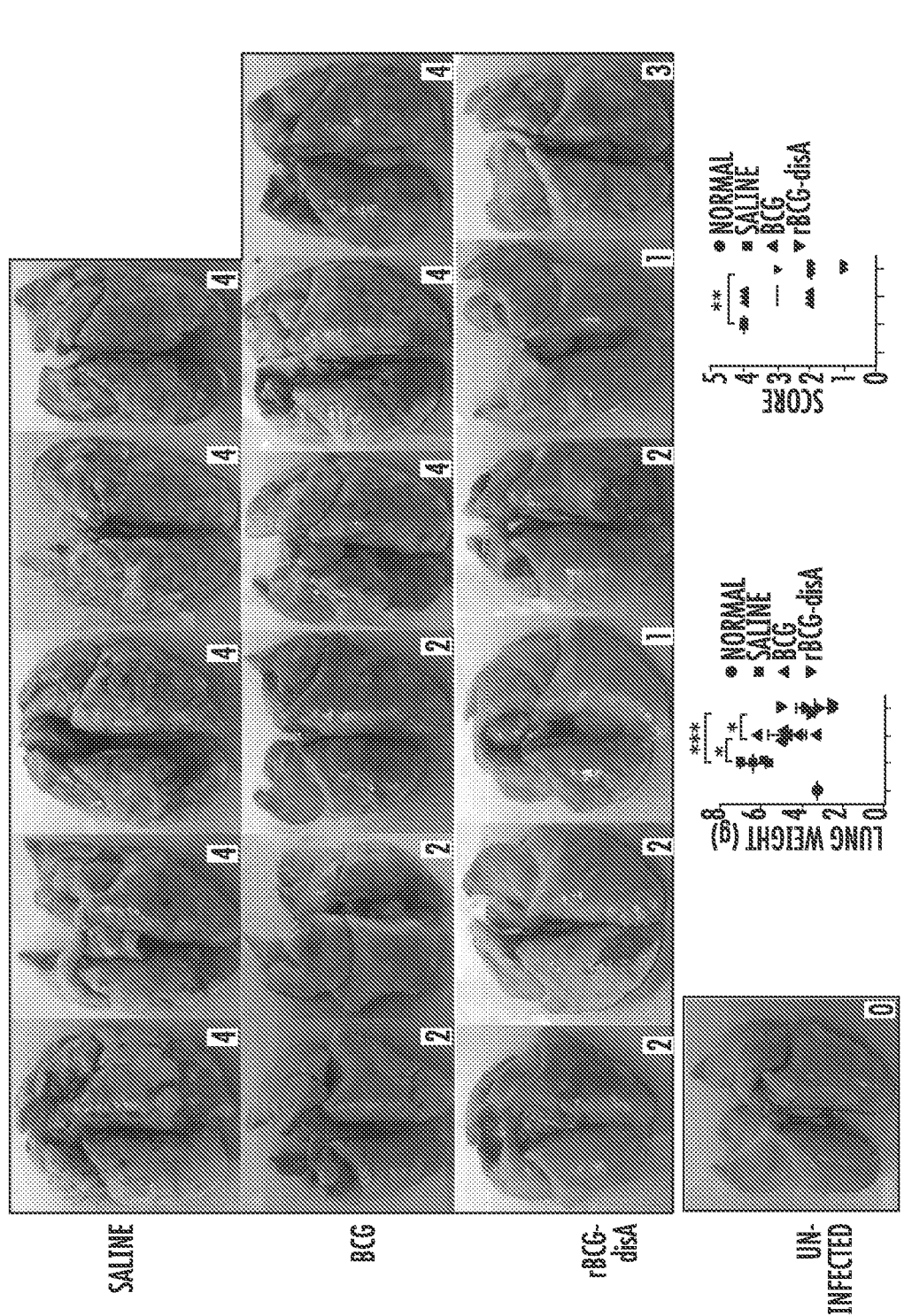
FIG. 21 illustrates the gross pathology of lungs 18 weeks post-infection of the guinea pigs described in FIG. 18.
Figure 22:
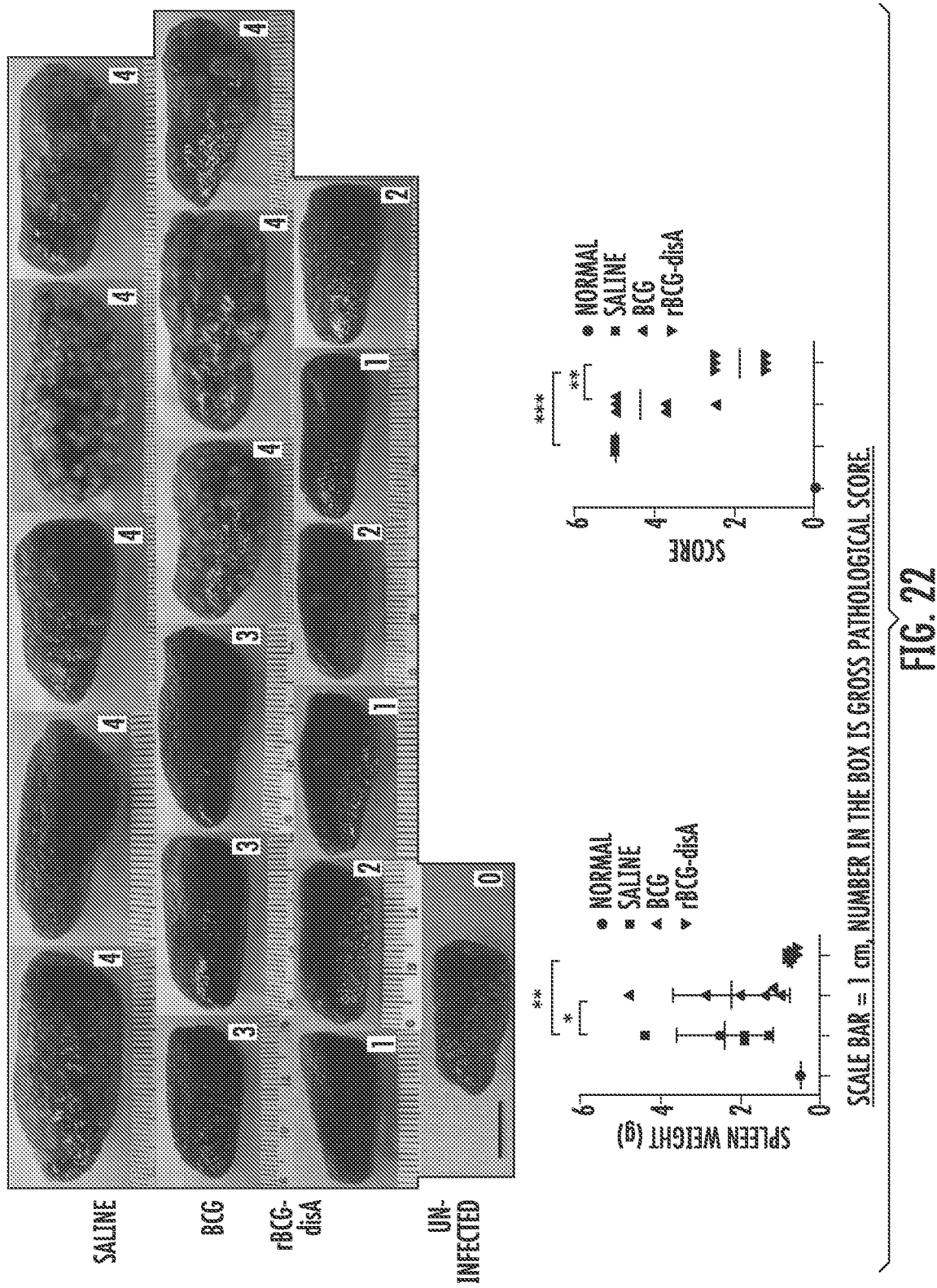
FIG. 22 illustrates the gross pathology of spleen 18 weeks post-infection of the guinea pigs described in FIG. 18.

Next, we investigated whether enhanced macrophage autophagy might account for the attenuation of the c-di-AMP over-expressing *M. tuberculosis* strain Mtb-OE by examining the auto-phagosome membrane specific marker LC3 in *M. tuberculosis* infected J774.1 cells. Fluorescence confocal imaging demonstrated a considerably higher percentage of cells (~15%) exhibiting LC3 puncta formation in the case of the over expression c-di-AMP strain Mtb-OE infection compared to the wild type strain Mtb-CDC1551 (~10%) and the knock out strain Mtb-disA-KO which is c-di-AMP deficient (~6%) (FIG. 11 a, b). In addition, Western blot analysis of endogenous LC3 revealed an increase in conversion of LC3-I to LC3-II in the Mtb-OE infected cells, indicating hyper-activation of autophagy (FIG. 2c). We also observed a considerably higher percentage of cells exhibiting pTBK1 positivity suggesting activation of IRF pathway in the Mtb-OE infected J774.1 cells (FIG. 8). These observations strongly suggest that hyper-induction of autophagy by macrophages may be one of the contributing factors that restricts the intracellular growth of Mtb-OE strain.

The virulence and pathogenicity of the *M. tuberculosis* strains in mouse aerosol infection models were examined. Remarkably, compared to WT infection using strain Mtb-CDC1551 (median time to death [MTD] of 150 days), a significant increase in the survival of Mtb-OE infected mice (MTD 321 days) was observed. In contrast, the knock out strain Mtb-disA-KO which is c-di-AMP deficient showed reduced survival with an MTD of 77 days (FIG. 12a). Concomitantly, the Mtb-OE strain also exhibited growth attenuation as evidenced by significantly reduced lung and spleen bacillary loads (FIG. 12b, c). Gross and histo-pathological findings of mouse lungs and spleens correlated well with the bacterial organ burden observations (FIG. 12d, e). The lungs of Mtb-OE infected-mice showed significantly fewer and smaller tubercle-like lesions compared to other groups. Concordantly, while Mtb-CDC1551, Mtb-disA-KO, and Mtb-COMP strain-infected mice exhibited considerable splenomegaly, spleens of the Mtb-OE infected mice appeared normal in size (FIG. 12d). Altogether, these observations clearly demonstrate attenuation of virulence in the c-di-AMP over-expressing *M. tuberculosis* strain.

The mouse serum cytokine levels between these groups at an early stage of disease of 2 weeks post-infection were compared. Consistent with the in vitro studies in mouse and human cells, we observed increased IFN-β levels in the serum of Mtb-OE infected mice compared to the Mtb-CDC1551 and Mtb-disA-KO group (FIG. 12f). In addition, the Mtb-OE group exhibited significantly higher serum levels of TNF-α (FIG. 12g). Since Type I IFN (IFN-β) is known to counter-regulate Type II IFN (IFN-β) responses, we measured IFN-β levels in the serum of infected mice (FIG. 12h). A strong inverse relationship between IFN-β and IFN-γ in these mice corresponds to the ability of the *M. tuberculosis*-strains to produce c-di-AMP.

These studies revealed bacterial c-di-AMP levels are strongly associated with the immunopathological outcome of bacterial infection, including *M. tuberculosis*, in mice. Next, the host cytosolic sensors that may detect *M. tuberculosis*-derived c-di-AMP starting with helicase DDX41, a cytosolic DNA, and CDN receptor that signals via STING were examined. A shRNA-mediated knocked down of DDX41 using RAW-Blue™ ISG cells (InvivoGen) that allow colorimetric measurement of the induction of the IRF pathway was performed. Knockdown of DDX41 caused a significant defect in activation of the IRF pathway and reduced IFN-β induction following infection with all the *M. tuberculosis* strains (FIG. 9a, b, c). We also observed a significantly reduced TNF-α production by the DDX41 knock-down cells (FIG. 9d). These results suggest that DDX41 is a key pattern recognition receptor for both DNA and c-di-AMP, and that DDX41 regulates the induction of Type I IFNs as well as TNF-α following *M. tuberculosis* infection.

The contribution of STING to the c-di-AMP-mediated IFN-β response during *M. tuberculosis* infection was investigated. A partial knock-down of STING in human THP1 cells showed considerably lower IFN-β induction than control cells (FIG. 10). Moreover, all *M. tuberculosis* strains failed to activate the IRF pathway or induce IFN-β in mouse RAW 264.7 macrophage IRF reporter cells lacking STING (STING-KO) (FIG. 13a, b, c, d). However, LPS, which stimulates Type I IFN through STING-independent pathways, induced elevated IFN-β response even in STING-KO cells (FIG. 13a, b). These results confirm that, in addition to its role in bacterial DNA mediated responses, STING is an essential component for c-di-AMP-mediated activation of the IRF pathway during *M. tuberculosis* infection. Furthermore, infection of macrophages with *M. bovis* bacille Calmette-Guérin (BCG), which is known to lack the Esx-1 secretion system, also showed activation of the IRF pathway at levels 20-60% of those seen following infection with either the Mtb-CDC1551 or the Erdman strain, a WT *M. tuberculosis* strain considered to be highly virulent (FIG. 13a, b). Importantly, the c-di-AMP over-expressing *M. bovis* BCG strain (BCG-OE) produced a significantly higher IRF and IFN-β response than *M. bovis* BCG itself, thus strongly suggesting that bacterial-derived c-di-AMP gains access to the host cell cytosol despite the absence of an Esx-1 secretion system (FIG. 13a, b). These experiments indicate that, while contributory to overall type I IFN response, Esx-1 may not be essential for c-di-AMP-triggered IRF pathway activation. However, further studies with ESX-1 deleted *M. tuberculosis* strains may provide direct evidence for contribution of ESX-1 secretion system in c-di-AMP mediated responses during *M. tuberculosis* infection.

Next, the role of cGAS in the detection of bacterial c-di-AMP was examined. Primary BMDMs (FIG. 13e) and BMDCs (FIG. 4f) from WT and cGAS-KO mice22 were infected with these mycobacterial strains and then IFN-β protein levels were measured. While loss of cGAS resulted in a considerably reduced IFN-β response compared to cells with intact cGAS (WT), all c-di-AMP overproducing strains continued to show significantly higher induction of IFN-β in cGAS-KO cells compared to their respective WT mycobacterial strains (FIG. 13e, f). Further, both WT and cGAS-KO BMDMs produced comparable levels of IFN-β following stimulation with synthetic c-di-AMP (FIG. 13g). Real time RT-PCR for IFN-β in BMDCs further confirmed these results (FIG. 13h). These experiments show that while c-di-AMP is a key ligand for IFN-β induction irrespective of cGAS, a significant part of the overall IFN-β response during *M. tuberculosis* infection is cGAS dependent and hence is probably due to bacterial DNA.

The data thus revealed the involvement of c-di-AMP as an *M. tuberculosis* Pathogen Associated Molecular Pathway (PAMP) that triggers host cell IFN-β secretion and autophagy. Our findings, which employed multiple bacterial strains (including the wild type *M. tuberculosis* CDC1551 and Erdman strains, and *M. bovis* BCG) were each modified to overexpress c-di-AMP and a variety of host phagocytic cells including those defective in important mediators of the CSP (STING, DDX41, and cGAS), consistently demonstrated that c-di-AMP, not bacterial DNA alone, is a key mediator of Type I IFN responses. Supplementary Table 1 lists major differences in our methods compared with those of earlier studies and reveals that strain, host cell, and methodological differences may have allowed the importance of c-di-AMP to have been overlooked in earlier studies. The studies have shown that c-di-AMP enhances the induction of Type I IFN in subjects as well as several pro-inflammatory cytokines including IL1-α, TNF-α and IL-6 that are believed to play protective roles during bacterial infections such as a *M. tuberculosis* infection. The data illustrates that resistance to tuberculosis (TB) requires CSP-mediated detection of c-di-AMP produced by *M. tuberculosis* and that levels of c-di-AMP modulate the fate of infection. A di-adenylate cyclase (disA or dacA)[4] over-expressing *M. tuberculosis* strain was formed that secretes excess c-di-AMP and activates the interferon regulatory factor (IRF) pathway with enhanced levels of IFN-β, elicits increased macrophage autophagy, and exhibits significant attenuation in mice. c-di-AMP-mediated IFN-β induction during *M. tuberculosis* infection was shown to require stimulator of interferon genes (STING)[5]-signaling. c-di-AMP induction of IFN-β is independent of the cytosolic nucleic acid receptor cyclic-GMP-AMP (cGAMP) synthase (cGAS), but cGAS nevertheless contributes substantially to the overall IFN-β response to *M. tuberculosis* infection. The present invention demonstrates c-di-AMP to be a key mycobacterial pathogen associated molecular pattern (PAMP) driving host Type I IFN responses and autophagy. Modulating the levels of c-di-AMP in a subject will enhance the subject's immune response and may be used to treat disease including immune-deficient disease such as HIV and bacterial infections including TB.

Hence, in this study we generated a recombinant BCG that over-expresses diadenylate cyclase (disA) of *M. tuberculosis* (Rv3586) and tested the prophylactic potential of rBCG-disA as a vaccine in mouse and guinea pig model of aerosol *M. tuberculosis* infection and also tested its ability to induce Type I IFN response. BCG strains modified to over-express c-di-AMP exhibited marked improvement in protective immunity against tuberculosis as evidenced by marked reduction in lung and spleen bacillary load and reduced pathology in guinea pig and mouse models of infection. In addition, in vitro studies in RAW cells revealed that, a c-di-AMP over-expressing BCG strain (rBCG-disA) produced a significantly higher IRF activation and IFN-β response than BCG itself, suggesting that bacteria-derived c-di-AMP gains access to the host cell cytosol despite the absence of an ESX-1 protein secretion system in the BCG strain and can potentiate the ability of BCG to induce higher IFN-β response.

Methods In this study we generated a recombinant BCG that over-expresses diadenylate cyclase (disA) of *M. tuberculosis* (Rv3586) and tested the prophylactic potential of rBCG-disA as a vaccine in mouse and guinea pig model of aerosol *M. tuberculosis* infection and also tested its ability to induce Type I IFN response and dependence on STING (Stimulator of Interferon Genes) and cGAS (cyclic GAMP Synthase) signaling axis.

Results BCG strains modified to over-express c-di-AMP exhibited marked improvement in protective immunity against tuberculosis as evidenced by marked reduction in lung and spleen bacillary load and reduced pathology. In addition, in vitro studies in RAW cells revealed that, a c-di-AMP-over-expressing BCG strain (rBCG-disA) produced a significantly higher IRF activation and IFN-β response than BCG itself in a STING dependent and cGAS independent manner, suggesting that bacteria-derived c-di-AMP gains access to the host cell cytosol despite the absence of an ESX-1 protein secretion system in the BCG strain and can potentiate the ability of BCG to induce higher IFN-β response.

We hypothesized that over-production of c-di-AMP by BCG may offer a multi-pronged approach to tap the adjuvant potential of c-di-AMP to improve the protective potential of BCG via (i) enhancing the type I IFN and other pro-inflammatory cytokine responses compared to BCG; (ii) enhancing the intrinsic ability of BCG to cause DC maturation; (iii) enhancing over-all antigen presentation following BCG vaccination via induction of higher levels of autophagy and induction of co-stimulatory molecules by this rBCG. The method disclosed in the present invention depends on the over-production of c-di-AMP by rBCGdisAOE. The present invention thus, provides a novel way to improve the existing BCG vaccine intrinsically without the need of exogenous addition of cytokines or use of synthetic chemicals or nucleotide molecules.

The present invention provides an improved method of immunization against tuberculosis using recombinant BCG-disAOE (rBCG-disAOE). The method disclosed in the present invention depends on the over-production of c-di-AMP by rBCG-disAOE. *Mycobacterium bovis* BCG Pasteur strain over expressing disA (Rv3586) gene of *Mycobacterium tuberculosis* under the transcriptional control of a strong mycobacterial promoter hsp60 using mycobacterial vectors described (DasGupta, Jain et al. 1998; Dhar, Rao et al. 2000; Jain, Dey et al. 2008). In the present invention, the protective efficacy of rBCG was assessed in mouse and a highly susceptible guinea pig model against *M. tuberculosis* challenge by the aerosol route as described before (Jain, Dey et al. 2008; Dey, Jain et al. 2011).

Immunization of mouse with rBCG resulted in a significantly enhanced protection characterized by a marked reduction in bacillary load in lungs (1.162 $\log_{10}$) and spleen (0.72 $\log_{10}$) compared to sham-immunized mice at 10 weeks post-infection. However, at this time point differences in CFU were not significantly different from BCG. Further at 18 weeks pos-infection, the extent of reduction in lung CFU in case of rBCG-disAOE immunization was markedly greater when compared to sham (by 0.35 $\log_{10}$) and BCG (by 0.49 $\log_{10}$), immunized animals signifying greater protection against pulmonary disease. Most significant effect of rBCG immunization on disease control, both in terms of reduction in bacillary load and pathology was evident in guinea pig model of *M. tuberculosis* infection. Wherein, immunization with both BCG as well as with rBCG-disAOE resulted in a significant reduction in lung and spleen bacillary load, when compared to the saline treated animals at 14 weeks post infection along with marked improvement in disease pathology as evidenced by reduced organ weight and pathology scores. However, the extent of reduction in bacillary burden in case of rBCG-disAOE immunization was markedly greater (by 0.37 $\log_{10}$ in lung and 1.6 $\log_{10}$ in spleen), when compared to BCG immunized animals. Further, at 18 weeks post-infection along with a markedly reduced disease pathology, rBCG immunized animals exhibited a markedly reduced lung (by 2.49 $\log_{10}$) and spleen (by 4.68 $\log_{10}$) bacillary burden when compared to sham immunized animals. Most importantly, rBCG treated animals showed a marked improvement when compared to BCG treated animals both in terms of lung and spleen bacillary burden (by 1.9 $\log_{10}$ and 2.54 $\log_{10}$, respectively). [See attached Figures]

EXAMPLES

Bacterial strains, plasmids, cell lines and animals. In this study we used *Escherichia coli* strain DH5α, *M. tuberculosis* CDC1551, *M. tuberculosis* Erdman, *M. Bovis* bacillus Calmette-Guérin (BCG). FIG. 14 lists all the *Mycobacterium* strains and plasmids used in this study. Details on the transposon insertion mutant of *M. tuberculosis* for M13692 (*M. tuberculosis*-mutant JHU-3586, Rv3586) used in this study is available on the TARGET website of the Johns Hopkins University. Plasmid pSD5-hsp60 (mycobacteria—*E. coli* shuttle vector for protein expression in *M. tuberculosis* from the strong mycobacterial promoter, hsp60) was used for expression. Plasmid pMH94Hyg was used for complementation. Both *E. coli* and mycobacterial strains were grown from frozen glycerol stocks stored at −70° C. Murine macrophage cells J774.1, RAW 264.7—derived macrophages such as RAW-Blue ISG, RAW-Lucia ISG, RAW Lucia ISG-KO-STING (Sting knockout cells), human monocyte THP1-Dual, THP1-Blu ISG-KD-STING cells (all from InvivoGen) and primary BMDMs and BMDCs from C57BL/6J and cGAS-KO mouse were used for in vitro experiments. All cell lines are free of mycoplasma contamination. Female mouse strains BALB/c and C57BL/6J (Jackson laboratories), age 6-7 weeks, were used for comparative studies of bacterial virulence, pathogenicity and time to death. The experiments were approved by the Institutional Animal Care and Use Committees (IACUCs) of Johns Hopkins University.

Reagents. J774.1 cells were cultured in RPMI-GlutaMAX (Life Technologies) with 10% (vol/vol) heat-inactivated FBS (Life technologies). Variants of RAW264.7 and THP-1 cells were cultured as per the suppliers protocol (InvivoGen) in DMEM and RPMI-GlutaMAX, respectively (Life Technologies) with 10% heat-inactivated FBS. The following antibodies were used: antibody to DDX41 (anti-DDX41; G14; Santa Cruz Biotechnology Inc. 1:500); anti-LC3A/B (D3U4C, XP; Cell Signaling Technologies, 1:1,000); anti-STING (D2P2F; Cell Signaling Technologies, 1:1,000); anti-pTBK1 (Ser172, D52C2; Cell Signaling Technologies 1:1,000); anti-GAPDH (14C10, Cell Signaling Technologies, 1:2,000). Secondary antibody anti-rabbit conjugated to fluorochrome Alexa Fluor 488, DAPI (Life Technologies), c-di-AMP (BIOLOG Life Science Institute), c-di-UMP, puromycin, zeocin, blasticidin, Quanti-Blue, Quanti-Luc (InvivoGen), hygromycin (Roche) and kanamycin (Sigma-Aldrich).

Extraction of nucleotides from *M. tuberculosis* and detection and quantitation of c-di-AMP by LC-MS/MS/MRM. Nucleotide extraction for LC-MS/MS were carried out as described42. Briefly, *M. tuberculosis* was grown to mid-log phase and harvested by quick centrifugation followed by resuspension in extraction buffer containing acetonitrile and methanol and water (2:2:1) and cXMP as an internal technical control. After a 15-min incubation and subsequent boiling at 100° C. for 10 min, the mixture was cooled down and extracted after quick centrifugation. Extraction was repeated twice as described above. Pooled samples were vacuum dried and resuspended in distilled water followed by detection and quantitation by LC-MS/MS MRM. Briefly, the chromatographic separation was performed on a Series 200 HPLC system (Perkin Elmer Instruments) and the analyte detection was performed on an API 3000 triple quadrupole mass spectrometer equipped with an electrospray ionization (EST) source (Applied Biosystems Inc.) using MRM analysis in positive ionization mode. The following SRM transitions using a dwell time of 40 ms were detected: cXMP: +347.1/153 (quantifier), +341.7/136 (identifier) and c-di-AMP: +659.1/330.2 (quantifier) and +659/524 (identifier).

Extraction of nucleotides from macrophage cytoplasm and detection and quantitation of c-di-AMP by LC-MS/MS/MRM. J774.1 cells were cultured in RPMI medium with 10% heat-inactivated FBS. Infections were carried out in either resting or IFN-γ- and LPS-activated J774.1 cells in six-well plates in triplicate. For infection, early log-phase cultures of various *Mycobacterium tuberculosis* strains were washed and diluted appropriately to predefined concentrations in antibiotic-free RPMI and were added to the J774.1 cells at a precalibrated MOI. The infection was allowed to continue for 4 h, following which extracellular bacteria were removed by washing the infected cells with DPBS thoroughly. After 24 h of infection, supernatants were removed and adherent macrophages were washed carefully with DPBS. Macrophages were lysed with the addition of 1 ml of 0.025% SDS (at this concentration of SDS, bacteria is not lysed) to each of the wells. Released bacilli were subsequently separated by centrifugation followed by filtration through a 0.2-μm membrane filter, and bacteria-free pooled macrophage cytoplasmic extracts were used for extraction of nucleotides and subsequent analysis by LC-MS/MS as described above.

Overexpression of MT3692 in *M. tuberculosis*. The disA gene of *M. tuberculosis*, MT3692, was PCR-amplified from *M. tuberculosis* CDC1551 chromosomal DNA using gene-specific primers, pSD5hsp60.MT3692(F) and pSD5hsp60.MT3692(R). The amplicons were cloned into the Mycobacterial expression vector pSD5-hsp60 at the NdeI and MluI restriction sites. The resulting construct pSD5-hsp60-MT3692 was sequenced and subsequently used to transform *M. tuberculosis* CDC1551 and recombinant clones were selected against kanamycin and confirmed by colony PCR using kanamycin gene-specific primers. Overexpression of MT3692 in the Mtb-OE strain was further confirmed by RNA sequencing of the Mtb-OE strain and measurement of c-di-AMP by LC-MS-MRM. Overexpression of MT3692 in the *M. tuberculosis* Erdman and *M. bovis* BCG strains were carried out using the same plasmid.

Construction of MT3692 complementation strain. To complement the transposon mutant for MT3692, a 279-bp DNA fragment including the coding sequence of the MT3692 gene and 1,714 by of the 5' sequence (including the upstream gene in the operon and gene's native promoter) was amplified by PCR with primers OPE-MT3692(F) and OPE-MT3692(R) and cloned into an integration vector, pMH94Hyg, at an XbaI restriction site. The resulting construct, pMH94Hyg-MT3692, was subjected to nucleotide sequencing and subsequently used to transform the Mtb-disA-KO strain. Candidate Hygromycin resistant Mtb-COMP colonies were selected, confirmed by PCR using hygromycin genespecific primers and genomic DNA as template. Mtb-COMP clones were further confirmed by measurement of c-di-AMP by LC-MS/MRM method.

Infection of mice with *M. tuberculosis* and assessment of bacterial load, pathology and time to death. Four strains of *M. tuberculosis*, Mtb-disA-KO, Mtb-COMP, Mtb-OE and Mtb-WT were used to infect 6-7-week-old female C57BL/6J mice by the aerosol route in a Glascol inhalation exposure system (Glascol) with an inoculum that implanted ~3.0 Log 10 c.f.u. in the lungs at day 1 (n=3 mice in each group). Animals from a narrow range of weight and age groups were randomly allocated for infection with different bacterial strains. Eight mice from each group were subsequently sacrificed at 2, 4, 8 and 12 weeks after infection to determine the lung and spleen c.f.u. counts (n=4) and histopathology and immunology studies (n=4). Lung and spleen tissues were homogenized in their entirety in PBS and colonies were enumerated on selective 7H11 plates after 3-4 weeks of incubation at 37° C. The number of colonies were counted and expressed as log 10 c.f.u. per organ. All groups were coded during the experiments. For histopathology, whole lungs were fixed in 10% buffered formalin and sections of 5 μm in thickness from formalin fixed and paraffin embedded tissues were cut onto glass slides and stained with H&E for histopathological examination. For time to death assay 6-7-week-old female BALB/c mice (n=10 per group) were infected as described above with ~3.5 log 10 c.f.u. of various strains of *M. tuberculosis* and monitored until their death due to tuberculosis. All experiments were carried out according to the guidelines of the Institutional Animal Care and Use Committees (IACUCs) of Johns Hopkins University.

Infection of macrophages with *M. tuberculosis* and assay for IRF activation and IFN-b production. J774.1 cells were cultured in RPMI medium with 10% heat-inactivated FBS. Infections were carried out in either resting or IFN-γ- and LPS-activated J774.1. cells in 24-well plates in triplicate. For infection, early log-phase cultures of various *M. tuberculosis* strains were washed and diluted appropriately to predefined concentrations in antibiotic-free RPMI and were added to the J774.1 cells at a precalibrated MOI. The infection was allowed to continue for 4 h, following which extracellular bacteria were removed by washing the infected cells with DPBS thoroughly. Serial dilutions of the bacterial suspension and macrophage lysate were plated at day '0' in order to determine an accurate bacterial count of infection and phagocytized bacterial number. For enumeration of bacterial growth, at 1, 2 and 4 d after infection cells were harvested and lysed using 0.025% SDS. Appropriate dilutions of the lysates were then inoculated onto MB7H11 agar plates in duplicate and incubated at 37° C. for 3 weeks. The number of colonies was counted and expressed as log 10 c.f.u. per well. Investigators were blinded for c.f.u. analysis. Macrophage culture supernatants collected at the indicated time points were used for measurement of various cytokines by ELISA. For immunofluorescence and western blot detection of LC3, at 6 h after infection macrophage cells were washed thoroughly and either fixed in 4% paraformaldehyde in PBS followed by immunofluorescence staining or lysates were prepared in RIPA buffer (Cell Signaling Technologies) for western blotting. RAW-Blue ISG and RAW-Lucia ISG or RAW-Lucia ISG-KO-STING (InvivoGen) cells were derived from the murine RAW 264.7 macrophage cell line by stable integration of an interferon regulatory factor (IRF)-inducible secreted embryonic alkaline phosphatase (SEAP) and luciferase reporter constructs, respectively. These cells without prior activation were infected with various strains of *M. tuberculosis* with a pre-calibrated MOI of 1:5 for 4 h. After infection, extracellular bacteria were removed by washing the infected cells with DPBS thoroughly. After 18 h incubation in fresh DMEM, supernatants were collected for estimation of IRF induction by SEAP colorimetric assay using QUANTI-Blue reagent (InvivoGen) or Luminescence assay using QUANTI-Luc (InvivoGen) and for measurement of cytokines by ELISA. THP1-Dual cells (InvivoGen) were grown as per the suppliers recommendations. THP1-Dual cells were derived from the human THP-1 monocyte cell line by stable integration of two inducible reporter constructs, a new secreted luciferase reporter gene, under the control of an ISG54 (interferon-stimulated gene) minimal promoter in conjunction with five IFN-stimulated response elements and a SEAP reporter gene fused to five copies of the NF-kB consensus transcriptional response element and three copies of the c-Rel binding site. As a result, THP1-Dual cells allow the simultaneous study of the NF-kB pathway, by monitoring the activity of SEAP, and the IRF pathway, by assessing the activity of Lucia in culture supernatants. THP1-Blue ISG-KD-STING cells were generated from THP1-Blue ISG cells through knock-down of the STING gene, and they were cultured as per the supplier's recommendations (InvivoGen). Mouse primary BMDMs and BMDCs were cultured and infected with precalibrated MOIs as described above for immortalized cell lines.

shRNA-mediated interference. RAW Blue ISG (InvivoGen) cells were transfected with a pool of five lentiviral vectors carrying a target gene sequence for DDX41 or a control plasmid (pLKO.1) (Thermo Scientific). At 24 h after transfection, cells were selected by the addition of puromycin to the medium. For transfection Lipofectamine LTA Plus (Life Technologies) reagent was used as per the manufacturer's instructions. Knockdown of DDX41 was confirmed by western blotting.

ELISA. ELISAs for IFN-β, IFN-γ, IL-1α, IL-6 and TNF-α were performed with the macrophage cell culture supernatants and serum of infected mice by using mouse cytokine-specific ELISA kits (eBiosciences, Biolegend) as per manufacturers' instructions. In vitro macrophage culture experiments were carried out in triplicate and at least thrice. Serum from four mice in each group were assayed by ELISA for cytokine levels.

Western blot analysis. For immunoblot analysis, macrophage cells at predefined time points after infection were collected and lysed in RIPA lysis buffer (Cell Signaling Technologies) containing complete protease inhibitors (Roche). LC3, STING, DDX41 and GAPDH western immunoreactivity assays of macrophage lysates were performed using anti-mouse antibodies per the antibody provider's (Cell Signaling Technology). Densitometry analyses of the western blots were carried out with GelQuant software.

Two-color immunofluorescence and confocal microscopy. Immunofluorescence staining was carried out by serial incubation of fixed cells grown on culture slide chambers with LC3-specific antibody, (Cell Signaling Technology) followed by incubation with an isotype-specific, fluorochrome (Alexa Fluor 488)-labeled goat anti-rabbit antibody (A-11001; Molecular Probes). Nuclei were stained with DAPI. For imaging, we used an Olympus BX61 with Roper/Photometrics Coolsnap HQ fluorescence microscope and Zeiss LSM 510-meta, confocal laser-scanning microscope at the Johns Hopkins University core microscopy facility. Slidebook (Intelligent Imaging), ZenLite (Zeiss) and ImageJ (public domain software available from the US National institutes of Health) software were used for image acquisition and/or analysis. Investigators were blinded during analysis. For LC3 analysis a stringent threshold was set to define a 'puncta', such that only those cells that exhibited formation of large LC3 aggregates occupying an area >1 μm were considered as positive. Extent of autophagy induction is thus represented by the percentage of LC3-positive Real-time RT-qPCR. Twenty four hours after infection with different strains of M. tuberculosis, RNA was extracted using the RNeasy Plus Micro kit according to the manufacturer's protocol (Qiagen). RNA was reverse-transcribed using the iScript Reverse Transcription Supermix (Bio-Rad) containing oligo-dT and random primers. cDNA was used for real-time qPGR using 2× iQ SYBR Green Supermix and an iCycler (Bio-Rad). The primers for real-time RT-qPCR. The IFNβ mRNA expression levels were normalized to β-actin expression and fold induction was calculated by the ΔΔCT method relative to those of untreated cells.

Statistical analyses. For comparisons between groups. Student's t-test (two tailed), one-way ANOVA with Tukey's post-test and two-way ANOVA with Bonferroni post-test were used wherever appropriate. Differences were considered significant at at least P<0.05. For statistical analysis, we used Prism 5 software (Version 5.01; GraphPad Software Inc.).

What is claimed:

1. A pharmaceutical composition comprising:
   (i) a recombinant *Mycobacterium* comprising a *Mycobacterium* from a first strain comprising an expression vector encoding a di-adenylate cyclase enzyme from a second strain of *Mycobacterium*, and
   (ii) a pharmaceutically acceptable carrier.

2. The pharmaceutical composition of claim 1, wherein the first strain and the second strain of *Mycobacterium* are selected from the group consisting of *Mycobacterium tuberculosis* or *Mycobacterium* bovis *Mycobacterium bovis*, and *Mycobacterium bovis* Bacille Calmette Guerin (BCG).

3. The pharmaceutical composition of claim 1, wherein the first strain of *Mycobacterium* is *Mycobacterium bovis* BCG.

4. The pharmaceutical composition of claim 1, wherein the expression vector is a mycobacterial expression vector.

5. The pharmaceutical composition of claim 4, wherein the expression vector comprises a DNA sequence encoding a di-adenylate cyclase protein (DisA).

6. The pharmaceutical composition of claim 5, wherein the DNA sequence comprises a *M. tuberculosis* disA gene.

7. The pharmaceutical composition of claim 1, wherein the expression vector comprises a hsp60 promoter.

8. The pharmaceutical composition of claim 7, wherein the expression of di-adenylate cyclase enzyme is regulated by the hsp60 promoter.

9. A pharmaceutical composition comprising:
   (i) a recombinant *Mycobacterium* comprising a *Mycobacterium* from a first strain comprising an expression vector encoding a di-adenylate cyclase enzyme from a second strain of *Mycobacterium*,
   (ii) at least one compounds enhancing immunogenicity, and
   (iii) a pharmaceutically acceptable carrier.

10. The pharmaceutical composition of claim 9, wherein the first strain and the second strain of *Mycobacterium* are selected from the group consisting of *Mycobacterium tuberculosis*, *Mycobacterium bovis*, and *Mycobacterium bovis* Bacille Calmette Guerin (BCG).

11. The pharmaceutical composition of claim 10, wherein the first strain of *Mycobacterium* is *Mycobacterium bovis* BCG.

12. The pharmaceutical composition of claim 9, wherein the expression vector is a mycobacterial expression vector.

13. The pharmaceutical composition of claim 12, wherein the expression vector comprises a DNA sequence encoding a di-adenylate cyclase protein (DisA).

14. The pharmaceutical composition of claim 13, wherein the DNA sequence comprise a *M. tuberculosis* disA gene.

15. A The pharmaceutical composition of claim 9, wherein the expression vector comprises a hsp60 promoter.

16. The pharmaceutical composition of claim 9, wherein the at least one of more compounds enhancing immunogenicity is synthetic c-di-AMP.

17. The pharmaceutical composition of claim 9, wherein the at least one compounds enhancing immunogenicity is selected from the group consisting of mycobacterial DNA, IFN, and combinations thereof.

18. A method of stimulating an immune response in a subject against TB comprising administering to the subject an effective amount of the composition of claim 1.

19. The method of claim 18, wherein the strain of *Mycobacterium* is selected from the group consisting of *Mycobacterium tuberculosis, Mycobacterium bovis*, or a combination thereof.

20. The method of claim 19, wherein the strain of *Mycobacterium* is BCG.

21. The method of claim 18, wherein the expression vector is a mycobacterial expression vector.

22. The method of claim 21, wherein the expression vector comprises the DNA sequence of diadenylate cyclase (disA).

23. The method of claim 22, wherein the disA is that of *M. tuberculosis* (Rv3586).

24. The method of claim 18, wherein the expression vector comprises a hsp60 promoter.

25. The method of claim 24, wherein the expression of di-adenylate cyclase enzyme is regulated by the hsp60 promoter.

26. A method of stimulating an immune response in a subject against TB comprising administering to the subject and effective amount of the composition of claim 9.

27. The method of claim 26, wherein the strain of *Mycobacterium* is selected from the group consisting of *Mycobacterium tuberculosis, Mycobacterium bovis*, or a combination thereof.

28. The method of claim 27, wherein the strain of *Mycobacterium* is BCG.

29. The method of claim 26, wherein the over-expression is by a mycobacterial expression vector.

30. The method of claim 29, wherein the expression vector comprises the DNA sequence of diadenylate cyclase (disA).

31. The method of claim 30, wherein the disA is that of *M. tuberculosis* (Rv3586).

32. The method of claim 29, wherein the expression vector comprises a hsp60 promoter.

33. The method of claim 32, wherein the expression of di-adenylate cyclase enzyme is regulated by the hsp60 promoter.

34. The pharmaceutical composition of claim 1, wherein the second strain of *Mycobacterium* is *Mycobacterium tuberculosis*.

35. The pharmaceutical composition of claim 1, wherein the recombinant *Mycobacterium* strain has an increased expression of the di-adenylate cyclase enzyme as compared to the first strain of *Mycobacterium*.

36. The pharmaceutical composition of claim 9, wherein the second strain of *Mycobacterium* is *Mycobacterium tuberculosis*.

37. The pharmaceutical composition of claim 9, wherein the recombinant *Mycobacterium* strain has an increased expression of the di-adenylate cyclase enzyme as compared to the first strain of *Mycobacterium*.

38. A pharmaceutical composition comprising:
   (i) a recombinant *Mycobacterium* comprising a *Mycobacterium bovis* Bacille Calmette Guerin (BCG) comprising an expression vector encoding a di-adenylate cyclase enzyme from *Mycobacterium tuberculosis*, and
   (ii) a pharmaceutically acceptable carrier.

39. The pharmaceutical composition of claim 38, further comprising at least one compound enhancing immunogenicity.

* * * * *